(12) United States Patent
Cabiri

(10) Patent No.: US 9,878,091 B2
(45) Date of Patent: Jan. 30, 2018

(54) MOTION ACTIVATED SEPTUM PUNCTURING DRUG DELIVERY DEVICE

(71) Applicant: MEDIMOP Medical Projects Ltd., Ra'anana (IL)

(72) Inventor: Oz Cabiri, Macabim-Reut (IL)

(73) Assignee: MEDIMOP Medical Projects Ltd., Ra'anana (IL)

( * ) Notice: Subject to any disclaimer, the term of this patent is extended or adjusted under 35 U.S.C. 154(b) by 0 days.

(21) Appl. No.: 14/696,644

(22) Filed: Apr. 27, 2015

(65) Prior Publication Data

US 2015/0224253 A1    Aug. 13, 2015

Related U.S. Application Data

(63) Continuation of application No. 14/510,846, filed on Oct. 9, 2014, which is a continuation of application
(Continued)

(51) Int. Cl.
*A61M 5/142*    (2006.01)
*A61M 5/28*    (2006.01)
(Continued)

(52) U.S. Cl.
CPC .... *A61M 5/14248* (2013.01); *A61M 5/14566* (2013.01); *A61M 5/283* (2013.01);
(Continued)

(58) Field of Classification Search
CPC .. A61M 2005/14252; A61M 2005/208; A61M 5/2033; A61M 2005/2073;
(Continued)

(56) References Cited

U.S. PATENT DOCUMENTS 3,946,732 A    3/1976   Hurscham
3,994,295 A    11/1976   Wulff
(Continued)

FOREIGN PATENT DOCUMENTS

CN    101868273 A    10/2010
EP    0401179 A1    12/1990
(Continued)

OTHER PUBLICATIONS

U.S. Appl. No. 14/683,253 by Cabiri, filed Apr. 10, 2015.
(Continued)

*Primary Examiner* — Theodore Stigell
*Assistant Examiner* — Benjamin Koo
(74) *Attorney, Agent, or Firm* — Panitch Schwarze Belisario & Nadel LLP

(57) ABSTRACT

A method and apparatus are disclosed for delivery of a drug to a recipient. In some embodiments, the delivery apparatus may unseal a drug containing reservoir. In some embodiments, the delivery rate may be controlled and/or adjustable. Optionally the apparatus may be disposable. Optionally, the apparatus may have a low profile and/or be wearable and/or attachable to the recipient. Optionally, discharge of the drug and/or unsealing of the reservoir may be driven by a plunger moving parallel to the base of the apparatus. Optionally, the apparatus may release a hypodermic needle into the recipient. Optionally, release of the hypodermic needle may be in a direction non-parallel and/or orthogonal to the direction of movement of the plunger. Optionally, prior to release, the hypodermic needle may be preserved in an aseptic state by a needle opening septum sealing a needle opening. Optionally, upon release, the hypodermic needle may pierce the needle opening septum.

4 Claims, 15 Drawing Sheets

Related U.S. Application Data

No. 13/429,942, filed on Mar. 26, 2012, now Pat. No. 9,463,280.

(51) Int. Cl.

| | | |
|---|---|---|
| A61M 5/24 | (2006.01) | |
| A61M 5/145 | (2006.01) | |
| A61M 5/31 | (2006.01) | |
| A61M 5/158 | (2006.01) | |
| A61M 5/172 | (2006.01) | |
| A61J 1/14 | (2006.01) | |

(52) U.S. Cl.
CPC ........... *A61J 1/1406* (2013.01); *A61M 5/1452* (2013.01); *A61M 5/14244* (2013.01); *A61M 5/158* (2013.01); *A61M 5/172* (2013.01); *A61M 5/3146* (2013.01); *A61M 2005/14208* (2013.01); *A61M 2005/14252* (2013.01); *A61M 2005/14256* (2013.01); *A61M 2005/14268* (2013.01); *A61M 2005/14533* (2013.01); *A61M 2005/14573* (2013.01); *A61M 2005/1581* (2013.01); *A61M 2005/247* (2013.01); *A61M 2005/2474* (2013.01); *A61M 2205/123* (2013.01)

(58) Field of Classification Search
CPC ................ A61M 5/3287; A61M 5/283; A61M 2005/247; A61M 2005/142564
See application file for complete search history.

(56) References Cited

U.S. PATENT DOCUMENTS

| | | | |
|---|---|---|---|
| 4,167,663 | A | 9/1979 | Granzow, Jr. et al. |
| 4,273,122 | A | 6/1981 | Whitney et al. |
| 4,396,385 | A | 8/1983 | Kelly et al. |
| 4,601,702 | A | 7/1986 | Hudson |
| 4,634,426 | A | 1/1987 | Kamen |
| 4,886,499 | A | 12/1989 | Cirelli et al. |
| 4,919,596 | A | 4/1990 | Slate et al. |
| 4,950,235 | A | 8/1990 | Slate et al. |
| 4,950,246 | A | 8/1990 | Muller |
| 5,109,850 | A | 5/1992 | Blanco et al. |
| 5,131,816 | A | 7/1992 | Brown et al. |
| 5,254,096 | A | 10/1993 | Rondelet et al. |
| 5,342,313 | A | 8/1994 | Campbell et al. |
| 5,354,287 | A | 10/1994 | Wacks |
| 5,383,865 | A | 1/1995 | Michel |
| 5,411,482 | A | 5/1995 | Campbell |
| 5,501,665 | A | 3/1996 | Jhuboo et al. |
| 5,558,639 | A | 9/1996 | Gangemi |
| 5,593,390 | A | 1/1997 | Castellano et al. |
| 5,616,132 | A | 4/1997 | Newman |
| 5,643,218 | A | 7/1997 | Lynn et al. |
| 5,647,853 | A | 7/1997 | Feldmann et al. |
| 5,658,133 | A | 8/1997 | Anderson et al. |
| 5,690,618 | A | 11/1997 | Smith et al. |
| D393,314 | S | 4/1998 | Meisner et al. |
| 5,800,420 | A | 9/1998 | Gross et al. |
| 5,807,375 | A | 9/1998 | Gross et al. |
| 5,814,020 | A | 9/1998 | Gross |
| 5,851,197 | A | 12/1998 | Marano et al. |
| 5,858,001 | A | 1/1999 | Tsals et al. |
| 5,858,008 | A | 1/1999 | Capaccio |
| 5,931,814 | A | 8/1999 | Alex et al. |
| 5,957,895 | A | 9/1999 | Sage et al. |
| 5,993,423 | A | 11/1999 | Choi |
| 5,997,501 | A | 12/1999 | Gross et al. |
| 6,004,297 | A | 12/1999 | Steenfeldt-Jensen et al. |
| 6,064,797 | A | 5/2000 | Crittendon et al. |
| 6,074,369 | A | 6/2000 | Sage et al. |
| 6,175,688 | B1 | 1/2001 | Cassidy et al. |
| 6,186,982 | B1 | 2/2001 | Gross et al. |
| 6,200,289 | B1 | 3/2001 | Hochman et al. |
| 6,248,093 | B1 | 6/2001 | Moberg |
| 6,277,095 | B1 | 8/2001 | Kriesel et al. |
| 6,277,098 | B1 | 8/2001 | Klitmose et al. |
| 6,277,099 | B1 | 8/2001 | Strowe et al. |
| 6,287,283 | B1 | 9/2001 | Ljunggreen et al. |
| 6,362,591 | B1 | 3/2002 | Moberg |
| 6,391,005 | B1 | 5/2002 | Lum et al. |
| 6,423,029 | B1 | 7/2002 | Elsberry |
| 6,423,035 | B1 | 7/2002 | Das et al. |
| D465,026 | S | 10/2002 | May et al. |
| 6,458,102 | B1 | 10/2002 | Mann et al. |
| 6,485,461 | B1 | 11/2002 | Mason et al. |
| 6,485,465 | B2 | 11/2002 | Moberg et al. |
| 6,500,150 | B1 | 12/2002 | Gross et al. |
| 6,517,517 | B1 | 2/2003 | Farrugia et al. |
| D471,274 | S | 3/2003 | Diaz et al. |
| D471,983 | S | 3/2003 | Hippolyte et al. |
| 6,530,901 | B1 | 3/2003 | Tsukada et al. |
| 6,555,986 | B2 | 4/2003 | Moberg |
| 6,558,351 | B1 | 5/2003 | Steil et al. |
| 6,589,229 | B1 | 7/2003 | Connelly et al. |
| 6,595,956 | B1 | 7/2003 | Gross et al. |
| 6,595,960 | B2 | 7/2003 | West et al. |
| 6,645,181 | B1 | 11/2003 | Lavi et al. |
| 6,652,482 | B2 | 11/2003 | Hochman |
| 6,656,158 | B2 | 12/2003 | Mahoney et al. |
| 6,656,159 | B2 | 12/2003 | Flaherty |
| 6,659,980 | B2 | 12/2003 | Moberg et al. |
| 6,673,033 | B1 | 1/2004 | Sciulli et al. |
| 6,679,862 | B2 | 1/2004 | Diaz et al. |
| 6,699,218 | B2 | 3/2004 | Flaherty et al. |
| 6,749,587 | B2 | 6/2004 | Flaherty |
| 6,768,425 | B2 | 7/2004 | Flaherty et al. |
| 6,786,890 | B2 | 9/2004 | Preuthun et al. |
| 6,800,071 | B1 | 10/2004 | McConnell et al. |
| 6,805,687 | B2 | 10/2004 | Dextradeur et al. |
| 6,824,529 | B2 | 11/2004 | Gross et al. |
| 6,843,782 | B2 | 1/2005 | Gross et al. |
| 6,854,620 | B2 | 2/2005 | Ramey |
| 6,905,298 | B1 | 6/2005 | Haring |
| 6,908,452 | B2 | 6/2005 | Diaz et al. |
| 6,933,693 | B2 | 8/2005 | Schuchmann |
| 6,950,028 | B2 | 9/2005 | Zweig |
| 6,960,192 | B1 | 11/2005 | Flaherty et al. |
| 7,001,360 | B2 | 2/2006 | Veasey et al. |
| 7,048,715 | B2 | 5/2006 | Diaz et al. |
| 7,060,059 | B2 | 6/2006 | Keith et al. |
| 7,128,727 | B2 | 10/2006 | Flaherty et al. |
| 7,144,384 | B2 | 12/2006 | Gorman et al. |
| 7,193,521 | B2 | 3/2007 | Moberg et al. |
| D544,092 | S | 6/2007 | Lewis |
| 7,247,149 | B2 | 7/2007 | Beyerlein |
| 7,250,037 | B2 | 7/2007 | Shermer et al. |
| 7,267,669 | B2 | 9/2007 | Staunton et al. |
| 7,303,549 | B2 | 12/2007 | Flaherty et al. |
| 7,390,314 | B2 | 6/2008 | Stutz, Jr. et al. |
| 7,407,493 | B2 | 8/2008 | Cane' |
| 7,455,663 | B2 | 11/2008 | Bikovsky |
| 7,459,571 | B2 | 12/2008 | Schlitter et al. |
| 7,465,290 | B2 | 12/2008 | Reilly |
| 7,497,842 | B2 | 3/2009 | Diaz et al. |
| 7,524,304 | B2 | 4/2009 | Genosar |
| 7,530,964 | B2 | 5/2009 | Lavi et al. |
| 7,547,281 | B2 | 6/2009 | Hayes et al. |
| 7,563,253 | B2* | 7/2009 | Tanner .................... A61M 5/24 604/232 |
| 7,565,208 | B2 | 7/2009 | Harris et al. |
| 7,569,050 | B2 | 8/2009 | Moberg et al. |
| D600,341 | S | 9/2009 | Loerwald |
| 7,585,287 | B2 | 9/2009 | Bresina et al. |
| 7,588,559 | B2 | 9/2009 | Aravena et al. |
| D602,155 | S | 10/2009 | Foley et al. |
| D602,586 | S | 10/2009 | Foley et al. |
| D604,835 | S | 11/2009 | Conley |
| 7,621,893 | B2 | 11/2009 | Moberg et al. |
| 7,628,770 | B2 | 12/2009 | Ethelfeld |
| 7,628,772 | B2 | 12/2009 | McConnell et al. |
| 7,628,782 | B2 | 12/2009 | Adair et al. |

(56) References Cited

U.S. PATENT DOCUMENTS

| | | |
|---|---|---|
| 7,637,891 B2 | 12/2009 | Wall |
| 7,641,649 B2 | 1/2010 | Moberg et al. |
| 7,660,627 B2 | 2/2010 | McNichols et al. |
| 7,678,079 B2 | 3/2010 | Shermer et al. |
| 7,682,338 B2 | 3/2010 | Griffin |
| 7,686,787 B2 | 3/2010 | Moberg et al. |
| 7,699,829 B2 | 4/2010 | Harris et al. |
| 7,699,833 B2 | 4/2010 | Moberg et al. |
| 7,704,227 B2 | 4/2010 | Moberg et al. |
| 7,704,231 B2 | 4/2010 | Pongpairochana et al. |
| 7,708,717 B2 | 5/2010 | Estes et al. |
| 7,713,238 B2 | 5/2010 | Mernoe |
| 7,713,240 B2 | 5/2010 | Istoc et al. |
| 7,717,913 B2 | 5/2010 | Novak et al. |
| 7,722,574 B2 | 5/2010 | Toman et al. |
| 7,736,344 B2 | 6/2010 | Moberg et al. |
| 7,744,589 B2 | 6/2010 | Mounce et al. |
| 7,749,194 B2 | 7/2010 | Edwards et al. |
| 7,753,879 B2 | 7/2010 | Mernoe |
| 7,766,873 B2 | 8/2010 | Moberg et al. |
| 7,776,030 B2 | 8/2010 | Estes et al. |
| 7,780,636 B2 | 8/2010 | Radmer et al. |
| 7,780,637 B2 | 8/2010 | Jerde et al. |
| 7,789,857 B2 | 9/2010 | Moberg et al. |
| 7,789,862 B2 | 9/2010 | Thorne, Jr. |
| 7,801,599 B2 | 9/2010 | Young et al. |
| 7,806,868 B2 | 10/2010 | De Polo et al. |
| 7,815,622 B2 | 10/2010 | Istoc et al. |
| 7,828,528 B2 | 11/2010 | Estes et al. |
| 7,837,659 B2 | 11/2010 | Bush, Jr. et al. |
| 7,846,132 B2 | 12/2010 | Gravesen et al. |
| 7,857,131 B2 | 12/2010 | Vedrine |
| 7,879,025 B2 | 2/2011 | Jacobson et al. |
| 7,879,026 B2 | 2/2011 | Estes et al. |
| 7,892,206 B2 | 2/2011 | Moberg et al. |
| 7,918,825 B2 | 4/2011 | O'Connor et al. |
| 7,918,843 B2 | 4/2011 | Genosar et al. |
| 7,935,104 B2 | 5/2011 | Yodfat et al. |
| 7,935,105 B2 | 5/2011 | Miller et al. |
| 7,938,803 B2 | 5/2011 | Mernoe et al. |
| 7,955,305 B2 | 6/2011 | Moberg et al. |
| 7,967,784 B2 | 6/2011 | Pongpairochana et al. |
| 7,981,105 B2 | 7/2011 | Adair et al. |
| 7,988,683 B2 | 8/2011 | Adair et al. |
| 7,993,300 B2 | 8/2011 | Nyholm et al. |
| 7,998,111 B2 | 8/2011 | Moberg et al. |
| 8,021,357 B2 | 9/2011 | Tanaka et al. |
| 8,025,658 B2 | 9/2011 | Chong et al. |
| 8,029,469 B2 | 10/2011 | Ethelfeld |
| 8,034,019 B2 | 10/2011 | Nair et al. |
| 8,038,666 B2 | 10/2011 | Triplett et al. |
| 8,057,436 B2 | 11/2011 | Causey et al. |
| 8,062,253 B2 | 11/2011 | Nielsen et al. |
| 8,062,257 B2 | 11/2011 | Moberg et al. |
| 8,065,096 B2 | 11/2011 | Moberg et al. |
| 8,066,694 B2 | 11/2011 | Wagener |
| D650,079 S | 12/2011 | Presta et al. |
| D652,503 S | 1/2012 | Cameron et al. |
| 8,105,279 B2 | 1/2012 | Mernoe et al. |
| 8,114,046 B2 | 2/2012 | Covino et al. |
| 8,114,064 B2 | 2/2012 | Alferness et al. |
| 8,114,066 B2 | 2/2012 | Naef et al. |
| 8,147,446 B2 | 4/2012 | Yodfat et al. |
| 8,152,764 B2 | 4/2012 | Istoc et al. |
| 8,152,770 B2 | 4/2012 | Reid |
| 8,152,779 B2 | 4/2012 | Cabiri |
| 8,152,793 B2 | 4/2012 | Keinanen et al. |
| 8,157,693 B2 | 4/2012 | Waksmundzki |
| 8,157,769 B2 | 4/2012 | Cabiri |
| 8,162,923 B2 | 4/2012 | Adams et al. |
| 8,167,841 B2 | 5/2012 | Teisen-Simony et al. |
| 8,172,804 B2 | 5/2012 | Bikovsky |
| 8,182,447 B2 | 5/2012 | Moberg et al. |
| 8,182,462 B2 | 5/2012 | Istoc et al. |
| 8,197,444 B1 | 6/2012 | Bazargan et al. |
| 8,206,351 B2 | 6/2012 | Sugimoto et al. |
| 8,267,893 B2 | 9/2012 | Moberg et al. |
| 8,267,921 B2 | 9/2012 | Yodfat et al. |
| 8,287,520 B2 | 10/2012 | Drew et al. |
| 8,308,679 B2 | 11/2012 | Hanson et al. |
| 8,348,898 B2 * | 1/2013 | Cabiri ............... A61M 5/14248 604/137 |
| 8,372,039 B2 | 2/2013 | Mernoe et al. |
| 8,373,421 B2 | 2/2013 | Lindegger et al. |
| 8,409,142 B2 | 4/2013 | Causey et al. |
| 8,414,557 B2 | 4/2013 | Istoc et al. |
| 8,430,847 B2 | 4/2013 | Mernoe et al. |
| 8,469,942 B2 | 6/2013 | Kow et al. |
| 8,474,332 B2 | 7/2013 | Bente, IV et al. |
| 8,475,408 B2 | 7/2013 | Mernoe et al. |
| 8,479,595 B2 | 7/2013 | Vazquez et al. |
| 8,483,980 B2 | 7/2013 | Moberg et al. |
| 8,495,918 B2 | 7/2013 | Bazargan et al. |
| 8,512,287 B2 | 8/2013 | Cindrich et al. |
| 8,517,987 B2 | 8/2013 | Istoc et al. |
| 8,523,803 B1 | 9/2013 | Favreau |
| 8,556,856 B2 | 10/2013 | Bazargan et al. |
| 8,574,216 B2 | 11/2013 | Istoc et al. |
| 8,603,026 B2 | 12/2013 | Favreau |
| 8,603,027 B2 | 12/2013 | Favreau |
| 8,617,110 B2 | 12/2013 | Moberg et al. |
| 8,628,510 B2 | 1/2014 | Bazargan et al. |
| 8,647,074 B2 | 2/2014 | Moberg et al. |
| 8,647,296 B2 | 2/2014 | Moberg et al. |
| 8,668,672 B2 | 3/2014 | Moberg et al. |
| 8,674,288 B2 | 3/2014 | Hanson et al. |
| 8,679,060 B2 | 3/2014 | Mernoe et al. |
| 8,681,010 B2 | 3/2014 | Moberg et al. |
| 8,690,855 B2 | 4/2014 | Alderete, Jr. et al. |
| 8,708,961 B2 | 4/2014 | Field et al. |
| 8,751,237 B2 | 6/2014 | Kubota |
| 8,753,326 B2 | 6/2014 | Chong et al. |
| 8,753,331 B2 | 6/2014 | Murphy |
| 8,764,707 B2 | 7/2014 | Moberg et al. |
| 8,764,723 B2 | 7/2014 | Chong et al. |
| 8,771,222 B2 | 7/2014 | Kanderian, Jr. et al. |
| 8,777,896 B2 | 7/2014 | Starkweather et al. |
| 8,777,924 B2 | 7/2014 | Kanderian, Jr. et al. |
| 8,777,925 B2 | 7/2014 | Patton |
| 8,784,369 B2 | 7/2014 | Starkweather et al. |
| 8,784,370 B2 | 7/2014 | Lebel et al. |
| 8,790,295 B1 | 7/2014 | Sigg et al. |
| 8,795,224 B2 | 8/2014 | Starkweather et al. |
| 8,795,231 B2 | 8/2014 | Chong et al. |
| 8,795,260 B2 | 8/2014 | Drew |
| 8,801,668 B2 | 8/2014 | Ali et al. |
| 8,810,394 B2 | 8/2014 | Kalpin |
| 9,463,280 B2 * | 10/2016 | Cabiri ............... A61M 5/14566 |
| 2002/0040208 A1 | 4/2002 | Flaherty et al. |
| 2002/0043951 A1 | 4/2002 | Moberg |
| 2002/0055711 A1 | 5/2002 | Lavi et al. |
| 2003/0135159 A1 | 7/2003 | Daily et al. |
| 2003/0160683 A1 | 8/2003 | Blomquist |
| 2003/0171717 A1 | 9/2003 | Farrugia et al. |
| 2003/0199825 A1 | 10/2003 | Flaherty |
| 2004/0085215 A1 | 5/2004 | Moberg et al. |
| 2004/0092873 A1 | 5/2004 | Moberg |
| 2004/0116866 A1 | 6/2004 | Gorman et al. |
| 2004/0260233 A1 | 12/2004 | Garibotto et al. |
| 2005/0065472 A1 | 3/2005 | Cindrich et al. |
| 2005/0070845 A1 | 3/2005 | Faries et al. |
| 2005/0071487 A1 | 3/2005 | Lu et al. |
| 2005/0171512 A1 | 8/2005 | Flaherty |
| 2005/0177136 A1 | 8/2005 | Miller |
| 2005/0197650 A1 | 9/2005 | Sugimoto et al. |
| 2005/0238507 A1 | 10/2005 | Dilanni et al. |
| 2005/0258714 A1 | 11/2005 | Henderson et al. |
| 2006/0095014 A1 | 5/2006 | Ethelfeld |
| 2006/0122577 A1 | 6/2006 | Poulsen et al. |
| 2006/0173408 A1 | 8/2006 | Wyrick |
| 2006/0173439 A1 | 8/2006 | Thorne et al. |
| 2006/0184154 A1 | 8/2006 | Moberg et al. |
| 2006/0229569 A1 | 10/2006 | Lavi et al. |
| 2006/0264890 A1 | 11/2006 | Moberg et al. |

(56) References Cited

U.S. PATENT DOCUMENTS

| | | |
|---|---|---|
| 2006/0283465 A1 | 12/2006 | Nickel et al. |
| 2007/0021733 A1 | 1/2007 | Hansen et al. |
| 2007/0049865 A1 | 3/2007 | Radmer et al. |
| 2007/0118405 A1 | 5/2007 | Campbell et al. |
| 2007/0149926 A1 | 6/2007 | Moberg et al. |
| 2007/0167912 A1 | 7/2007 | Causey et al. |
| 2007/0191770 A1 | 8/2007 | Moberg et al. |
| 2007/0219480 A1 | 9/2007 | Kamen et al. |
| 2007/0282269 A1 | 12/2007 | Carter et al. |
| 2008/0033369 A1 | 2/2008 | Kohlbrenner et al. |
| 2008/0051710 A1* | 2/2008 | Moberg ............... A61J 1/1406 604/131 |
| 2008/0051711 A1 | 2/2008 | Mounce et al. |
| 2008/0051727 A1 | 2/2008 | Moberg et al. |
| 2008/0059133 A1 | 3/2008 | Edwards et al. |
| 2008/0125700 A1 | 5/2008 | Moberg et al. |
| 2008/0140006 A1 | 6/2008 | Eskuri et al. |
| 2008/0140018 A1 | 6/2008 | Enggaard et al. |
| 2008/0147004 A1 | 6/2008 | Mann et al. |
| 2008/0156476 A1 | 7/2008 | Smisson |
| 2008/0167641 A1 | 7/2008 | Hansen et al. |
| 2008/0188813 A1 | 8/2008 | Miller et al. |
| 2008/0215006 A1 | 9/2008 | Thorkild |
| 2008/0221522 A1 | 9/2008 | Moberg et al. |
| 2008/0221523 A1 | 9/2008 | Moberg et al. |
| 2008/0269723 A1 | 10/2008 | Mastrototaro et al. |
| 2008/0294143 A1 | 11/2008 | Tanaka et al. |
| 2008/0306449 A1 | 12/2008 | Kristensen et al. |
| 2008/0312601 A1 | 12/2008 | Cane |
| 2008/0319416 A1 | 12/2008 | Yodfat et al. |
| 2009/0054750 A1 | 2/2009 | Jennewine |
| 2009/0076453 A1 | 3/2009 | Mejlhede et al. |
| 2009/0088694 A1 | 4/2009 | Carter et al. |
| 2009/0088731 A1 | 4/2009 | Campbell et al. |
| 2009/0093792 A1 | 4/2009 | Gross et al. |
| 2009/0093793 A1* | 4/2009 | Gross ............... A61M 5/14566 604/518 |
| 2009/0124977 A1 | 5/2009 | Jensen |
| 2009/0149830 A1 | 6/2009 | Spector |
| 2009/0182277 A1 | 7/2009 | Carter |
| 2009/0234319 A1 | 9/2009 | Marksteiner |
| 2009/0240240 A1 | 9/2009 | Hines et al. |
| 2009/0253973 A1 | 10/2009 | Bashan et al. |
| 2009/0259176 A1 | 10/2009 | Yairi |
| 2009/0299397 A1 | 12/2009 | Ruan et al. |
| 2009/0326509 A1 | 12/2009 | Muse et al. |
| 2010/0030156 A1 | 2/2010 | Beebe et al. |
| 2010/0030198 A1 | 2/2010 | Beebe et al. |
| 2010/0037680 A1 | 2/2010 | Moberg et al. |
| 2010/0049144 A1 | 2/2010 | McConnell et al. |
| 2010/0057057 A1 | 3/2010 | Hayter et al. |
| 2010/0076412 A1 | 3/2010 | Rush et al. |
| 2010/0094255 A1 | 4/2010 | Nycz et al. |
| 2010/0100076 A1 | 4/2010 | Rush et al. |
| 2010/0100077 A1 | 4/2010 | Rush et al. |
| 2010/0106098 A1 | 4/2010 | Atterbury et al. |
| 2010/0121314 A1 | 5/2010 | Iobbi |
| 2010/0137790 A1 | 6/2010 | Yodfat |
| 2010/0145303 A1 | 6/2010 | Yodfat et al. |
| 2010/0162548 A1 | 7/2010 | Leidig |
| 2010/0168607 A1 | 7/2010 | Miesel |
| 2010/0168683 A1* | 7/2010 | Cabiri ............... A61M 5/14248 604/263 |
| 2010/0198157 A1 | 8/2010 | Gyrn et al. |
| 2010/0204657 A1 | 8/2010 | Yodfat et al. |
| 2010/0217192 A1 | 8/2010 | Moberg et al. |
| 2010/0217193 A1 | 8/2010 | Moberg et al. |
| 2010/0234830 A1 | 9/2010 | Straessler et al. |
| 2010/0241065 A1 | 9/2010 | Moberg et al. |
| 2010/0264931 A1 | 10/2010 | Lindegger et al. |
| 2010/0274112 A1 | 10/2010 | Hoss et al. |
| 2010/0274192 A1 | 10/2010 | Mernoe |
| 2010/0276411 A1 | 11/2010 | Hansen et al. |
| 2010/0280499 A1 | 11/2010 | Yodfat et al. |
| 2010/0331826 A1 | 12/2010 | Field et al. |
| 2011/0034900 A1 | 2/2011 | Yodfat et al. |
| 2011/0054399 A1 | 3/2011 | Chong et al. |
| 2011/0054400 A1 | 3/2011 | Chong et al. |
| 2011/0060284 A1 | 3/2011 | Harr |
| 2011/0119033 A1 | 5/2011 | Moberg et al. |
| 2011/0160654 A1 | 6/2011 | Hanson et al. |
| 2011/0160666 A1 | 6/2011 | Hanson et al. |
| 2011/0160669 A1 | 6/2011 | Gyrn et al. |
| 2011/0172645 A1 | 7/2011 | Moga et al. |
| 2011/0178472 A1 | 7/2011 | Cabiri |
| 2011/0184342 A1 | 7/2011 | Pesach et al. |
| 2011/0201998 A1 | 8/2011 | Pongpairochana et al. |
| 2011/0224614 A1 | 9/2011 | Moberg et al. |
| 2011/0233393 A1 | 9/2011 | Hanson et al. |
| 2011/0238031 A1 | 9/2011 | Adair et al. |
| 2011/0245773 A1 | 10/2011 | Estes et al. |
| 2011/0264383 A1 | 10/2011 | Moberg et al. |
| 2011/0270160 A1 | 11/2011 | Mernoe |
| 2011/0282282 A1 | 11/2011 | Lorenzen et al. |
| 2011/0295205 A1 | 12/2011 | Kaufmann et al. |
| 2011/0313238 A1 | 12/2011 | Reichenbach et al. |
| 2011/0313351 A1 | 12/2011 | Kamen et al. |
| 2011/0319861 A1 | 12/2011 | Wilk |
| 2011/0319919 A1 | 12/2011 | Curry et al. |
| 2012/0004602 A1 | 1/2012 | Hanson et al. |
| 2012/0010594 A1 | 1/2012 | Holt et al. |
| 2012/0022499 A1 | 1/2012 | Anderson et al. |
| 2012/0025995 A1 | 2/2012 | Moberg et al. |
| 2012/0029431 A1 | 2/2012 | Hwang et al. |
| 2012/0035546 A1 | 2/2012 | Cabiri |
| 2012/0041364 A1 | 2/2012 | Smith |
| 2012/0041370 A1 | 2/2012 | Moberg et al. |
| 2012/0041414 A1 | 2/2012 | Estes et al. |
| 2012/0071828 A1 | 3/2012 | Tojo et al. |
| 2012/0096953 A1 | 4/2012 | Bente, IV et al. |
| 2012/0096954 A1 | 4/2012 | Vazquez et al. |
| 2012/0101436 A1 | 4/2012 | Bazargan et al. |
| 2012/0108933 A1 | 5/2012 | Liang et al. |
| 2012/0160033 A1 | 6/2012 | Kow et al. |
| 2012/0165733 A1 | 6/2012 | Bazargan et al. |
| 2012/0165780 A1 | 6/2012 | Bazargan et al. |
| 2012/0215169 A1 | 8/2012 | Moberg et al. |
| 2012/0215199 A1 | 8/2012 | Moberg et al. |
| 2012/0226234 A1 | 9/2012 | Bazargan et al. |
| 2012/0259282 A1 | 10/2012 | Alderete, Jr. et al. |
| 2012/0310153 A1 | 12/2012 | Moberg et al. |
| 2013/0068319 A1 | 3/2013 | Plumptre et al. |
| 2013/0096509 A1 | 4/2013 | Avery et al. |
| 2013/0133438 A1 | 5/2013 | Kow et al. |
| 2013/0175192 A1 | 7/2013 | Iio et al. |
| 2013/0218089 A1 | 8/2013 | Davies et al. |
| 2013/0218092 A1* | 8/2013 | Davies ............... A61M 5/32 604/192 |
| 2013/0237953 A1 | 9/2013 | Kow et al. |
| 2013/0245595 A1 | 9/2013 | Kow et al. |
| 2013/0253419 A1 | 9/2013 | Favreau |
| 2013/0253420 A1 | 9/2013 | Favreau |
| 2013/0253421 A1 | 9/2013 | Favreau |
| 2013/0331791 A1 | 12/2013 | Gross et al. |
| 2014/0055073 A1 | 2/2014 | Favreau |
| 2014/0055076 A1 | 2/2014 | Favreau |
| 2014/0058349 A1 | 2/2014 | Bazargan et al. |
| 2014/0083517 A1 | 3/2014 | Moia et al. |
| 2014/0094755 A1 | 4/2014 | Bazargan et al. |
| 2014/0128807 A1 | 5/2014 | Moberg et al. |
| 2014/0128835 A1 | 5/2014 | Moberg et al. |
| 2014/0135692 A1 | 5/2014 | Alderete, Jr. et al. |
| 2014/0135694 A1 | 5/2014 | Moberg et al. |
| 2014/0142499 A1 | 5/2014 | Moberg et al. |
| 2014/0148784 A1* | 5/2014 | Anderson ......... A61M 5/14248 604/506 |
| 2014/0148785 A1 | 5/2014 | Moberg et al. |
| 2014/0163522 A1 | 6/2014 | Alderete, Jr. et al. |
| 2014/0171881 A1 | 6/2014 | Cabiri |
| 2014/0194819 A1 | 7/2014 | Maule et al. |
| 2014/0207064 A1 | 7/2014 | Yavorsky |
| 2014/0207065 A1 | 7/2014 | Yavorsky |
| 2014/0207066 A1 | 7/2014 | Yavorsky |
| 2014/0210631 A1 | 7/2014 | Zavis |

(56) References Cited

U.S. PATENT DOCUMENTS

| | | | |
|---|---|---|---|
| 2014/0213975 A1 | 7/2014 | Clemente et al. | |
| 2014/0236087 A1 | 8/2014 | Alderete, Jr. et al. | |
| 2014/0261758 A1 | 9/2014 | Wlodarczyk et al. | |
| 2014/0288511 A1 | 9/2014 | Tan-Malecki et al. | |
| 2015/0011976 A1* | 1/2015 | Vouillamoz | A61M 5/2066 604/507 |
| 2016/0015910 A1 | 1/2016 | Mukai et al. | |

FOREIGN PATENT DOCUMENTS

| | | |
|---|---|---|
| EP | 0744975 A1 | 12/1996 |
| EP | 1666080 A1 | 6/2006 |
| EP | 2060606 A1 | 5/2009 |
| EP | 2345441 A1 | 7/2011 |
| EP | 2454483 B1 | 8/2015 |
| WO | 8911302 A1 | 11/1989 |
| WO | 9009202 A1 | 8/1990 |
| WO | 9521645 A1 | 8/1995 |
| WO | 9632975 A1 | 10/1996 |
| WO | 9721457 A1 | 6/1997 |
| WO | 9733638 A1 | 9/1997 |
| WO | 2007092618 A2 | 8/2007 |
| WO | 2007130868 A1 | 11/2007 |
| WO | 2008024810 A2 | 2/2008 |
| WO | 2008024814 A2 | 2/2008 |
| WO | 2008129549 A1 | 10/2008 |
| WO | 2009081262 A1 | 7/2009 |
| WO | 2011090955 A1 | 7/2011 |
| WO | 2011113806 A1 | 9/2011 |
| WO | 2012032411 A2 | 3/2012 |

OTHER PUBLICATIONS

Office Action dated May 18, 2015 in U.S. Appl. No. 13/429,942 by Cabiri.
U.S. Appl. No. 13/429,942 by Cabiri, filed Mar. 26, 2012.
U.S. Appl. No. 13/886,867 by Cabiri, filed May 3, 2013.
Int'l Search Report and Written Opinion dated Apr. 5, 2013 in Int'l Application No. PCT/US2012/050696.
Office Action dated Aug. 15, 2013 in U.S. Appl. No. 13/429,942 by Cabiri.
Office Action dated Jan. 16, 2014 in U.S. Appl. No. 13/429,942 by Cabiri.
Int'l Search Report and Written Opinion dated Jun. 30, 2014 in Int'l Application No. PCT/US2013/031598.
Int'l Search Report and Written Opinion dated Aug. 28, 2014 in Int'l Application No. PCT/US2014/035662.
Int'l Preliminary Report on Patentability dated Aug. 14, 2014 in Int'l Application No. PCT/US2012/050696.
U.S. Appl. No. 14/372,384 by Cabiri, filed Jul. 15, 2014.
Office Action dated Jan. 28, 2015 in U.S. Appl. No. 13/429,942 by Cabiri.
U.S. Appl. No. 14/593,041 by Cabiri, filed Jan. 9, 2015.
Office Action dated Apr. 19, 2016 in U.S. Appl. No. 14/372,384, by Cabiri.
Office Action dated May 17, 2016 in U.S. Appl. No. 13/886,867, by Cabiri.
Office Action dated Nov. 25, 2015 in U.S. Appl. No. 14/372,384 by Cabiri.
Office Action dated Oct. 28, 2015 in U.S. Appl. No. 13/429,942 by Cabiri.
Office Action dated Dec. 3, 2015 in CN Application No. 201280068544.0.
Office Action dated Feb. 24, 2016 in U.S. Appl. No. 13/429,942 by Cabiri.
Office Action dated Jun. 1, 2016 in CN Application No. 2013800274556.
Office Action dated Jun. 17, 2016 in CN Application No. 201280068544.0.
Office Action dated Feb. 15, 2017 in CN Application No. 2013800274556.
Office Action dated Jan. 17, 2017 in EP Application No. 13716886.
Office Action dated Sep. 8, 2017 is U.S. Appl. No. 15/510,846, by Aida.
Office Action dated Nov. 17, 2017 in U.S. Appl. No. 14/510,846, by Cabiri.
Office Action dated Nov. 14, 2017 in U.S. Appl. No. 14/593,041, by Cabiri.

* cited by examiner

MOTION ACTIVATED SEPTUM PUNCTURING DRUG DELIVERY DEVICE

CROSS REFERENCE TO RELATED APPLICATIONS

This application is a continuation of U.S. application Ser. No. 14/510,846, filed Oct. 9, 2014, entitled "Motion Activated Septum Puncturing Drug Delivery Device," which is a continuation of similarly-titled U.S. application Ser. No. 13/429,942, filed Mar. 26, 2012, now U.S. Pat. No. 9,463,280, the disclosure of each of which is incorporated herein by reference in its entirety.

BACKGROUND OF THE INVENTION

The present invention, in some embodiments thereof, relates to an apparatus wearable by a recipient and method for delivering a substance to a recipient, more particularly, but not exclusively, to an apparatus with a single-motion controlled-rate power train for sequentially unsealing a reservoir containing a drug and delivering the drug to a recipient.

U.S. Published Patent Application 2009/0093792 to the present author discloses an apparatus for administering a substance to a subject. A vial contains the substance and a stopper is disposed within the vial and is slidably coupled to the vial. A first threaded element is (a) rotatable with respect to the vial and (b) substantially immobile proximally with respect to the vial during rotation of the first threaded element. A second threaded element is threadedly coupled to the first threaded element. At least a distal end of the second threaded element is substantially non-rotatable with respect to the vial, and the distal end of the second threaded element defines a coupling portion that couples the second threaded element to the stopper. The first threaded element, by rotating, linearly advances the stopper and at least the distal end of the second threaded element toward a distal end of the vial. A vial piercing mechanism is movably (e.g., rotatably) coupled to a housing base. As part of the insertion of vial into the housing base, a seal at distal end of the vial is pierced by pressing the seal against the piercing mechanism. The substance is configured to subsequently flow through a tube toward an activation mechanism, which is typically coupled to the housing base, and is configured to insert a cannula and/or a needle through the subject's skin and to deliver the substance via the cannula and/or the needle.

U.S. Pat. No. 5,858,001 to Tsals discloses a liquid drug delivery device adapted to be adhered to the skin of a subject by a base member defining a skin-contacting surface having an adhesive coating. A columnar cartridge serves as reservoir for the drug and is incorporated in a housing which is connected to the base member such that in use the longitudinal axis of the cartridge is disposed substantially parallel to the skin-contacting surface. A delivery needle communicating in use with the interior of the cartridge penetrates the skin of the subject when the housing snaps downward relative to the base member. This action also causes the actuation of a citric acid/sodium bicarbonate gas generator which generates a gas to move a piston within the cartridge, compressing the drug compartment. This compression causes a stopper to be penetrated by a conduit in communication with the delivery needle, allowing the drug to be ejected from the compartment through the needle and into the subcutaneous tissue of the subject.

US Published Patent Application 2006/0173408 to Wyrick discloses a reloadable medicine injector and methods in which a barrel with a receiving cavity is adapted to slidably to receive a syringe subassembly for axial movement therein. Upon removal of a safety and release of a syringe driver, the syringe driver moves forward and injects the syringe needle. A plurality of penetration controls are shown for controlling injection needle penetration depth. In some embodiments, the injector makes use of a double needle assembly in which a double needle hub mounts a seal penetration needle that projects rearwardly toward a penetrable seal on the associated ampule. A flesh penetration needle projects forwardly. In practice, both needles can be made integral.

U.S. Pat. No. 5,997,501 to Gross discloses an intradermal drug delivery device comprising a housing having a drug reservoir therewithin. A microprocessor-controlled electrolytic cell provides gas to expand a gas generation chamber and thereby contract the reservoir. A hollow needle, communicating at an inner end thereof with the reservoir, extends from a lower surface of the housing such that contraction of the reservoir forces drug to escape therefrom via the needle. The device permits delivery of drugs of relatively large molecular weights at slow rates.

U.S. Published Patent Application 2011/0178472 and PCT Application WO 2011/090955 to the present author disclose a needle assembly adapted for fluid communication with a cartridge containing a substance to be delivered to a subject. The needle assembly characterized by a biasing device arranged to apply a biasing force on a needle to cause the needle to protrude outwards of a housing to pierce the subject, and biasing device release apparatus including a biasing device arrestor that initially blocks movement of the biasing device. After finishing the drug administration, the needle release apparatus lifted off the patient's body, which causes the safety latch to move back to the down position and the needle to be retracted back into the housing.

A safety latch position sensor is provided for sensing when safety latch moves to an up position indicating that the device has been attached to a patient. A controller initiates operation of an actuator after a predetermined time delay (e.g., 5-15 seconds) to ensure that the drug delivery apparatus was indeed placed on purpose on the patient for delivering the drug. When operated, the actuator rotates a shaft causing the biasing device arrestor to move linearly out of an aperture. As soon as the biasing device arrestor has moved out of the aperture, the biasing device is no longer blocked and it now pushes down on a needle piercing the patient's skin.

Additional background art includes U.S. Published Patent Applications 2011/0178472 to the same author, U.S. Pat. No. 7,789,862 to Thorne, U.S. Pat. No. 7,780,636 to Radmer, U.S. Pat. No. 5,957,895 to Sage, U.S. Pat. No. 7,918,843 to Genosar, and U.S. Pat. No. 7,789,862 to Thorne.

BRIEF SUMMARY OF THE INVENTION

According to an aspect of some embodiments of the present invention there is provided an apparatus wearable by a recipient having a single motion power train for sequentially unsealing a reservoir and delivering a drug to the recipient. The apparatus may include a seal of the reservoir. The apparatus may also include a controlled rate power source. The apparatus may also include a plunger driven by the controlled rate power source. The apparatus may also include a hollow needle. An initial movement of the plunger may drive the hollow needle through the seal and subsequent movement of the plunger may discharge the drug from the reservoir.

According to some embodiments of the invention, the controlled rate power source may include a direct current motor, a stepper motor and/or a linear actuator.

According to some embodiments of the invention, the apparatus may further include a surface configured for attaching to a skin of the recipient.

According to some embodiments of the invention, the apparatus may further include a pathway for movement of the reservoir. The initial movement of the plunger may impel the reservoir along the pathway.

According to some embodiments of the invention, the pathway may be substantially parallel to the surface.

According to some embodiments of the invention, the plunger may be configured for discharging a liquid having a viscosity of at least 10 centipoise.

According to some embodiments of the invention, the plunger may be configured for discharging at a substantially constant rate for at least 1 minute.

According to some embodiments of the invention, the reservoir may be configured for long term storage of the drug inside of the apparatus.

According to some embodiments of the invention, the apparatus may further include a hypodermic needle and a needle release for inserting the hypodermic needle into the recipient. The needle release may be synchronized to the plunger.

According to some embodiments of the invention, a direction of the needle release may be non-parallel to a direction of the movement of the plunger.

According to some embodiments of the invention, a direction of the needle release may be substantially orthogonal to a direction of the movement of the plunger.

According to some embodiments of the invention, the apparatus may further include a processor for controlling the controlled rate power source.

According to some embodiments of the invention, the apparatus may further include a septum located in a needle opening of the apparatus. Upon release of a hypodermic needle, the hypodermic needle may puncture the septum before being inserted into the recipient.

According to some embodiments of the invention, the apparatus may further include a rotation sensor. The controlling may be according to an output of the rotation sensor.

According to some embodiments of the invention, the apparatus may further include a rotation sensor. The processor may sense the puncturing of the seal based on an output of the rotation sensor.

According to some embodiments of the invention, the hollow needle may be initially in fluid communication with the reservoir. The seal may be configured for sealing the hollow needle.

According to some embodiments of the invention, the reservoir may include a cartridge insertable into the apparatus.

According to an aspect of some embodiments of the present invention there is provided a method for delivering a drug to a recipient with a delivery apparatus. The drug may be contained in a reservoir initially sealed by a seal for long term aseptic storage. The delivery apparatus may include a hollow needle and a plunger. The method may include attaching a surface of the delivery apparatus to the recipient. The method may also include applying a force with the plunger to a contents of the reservoir. The method may also include puncturing the seal with the hollow needle by the force. The method may also include discharging the drug from the reservoir by the force subsequent to the puncturing. The method may also include detecting a rate of the discharging, and the method may also include adjusting the rate of the discharging based on a result of the detecting.

According to some embodiments of the invention, the applying of the force may be in a direction substantially parallel to the surface.

According to some embodiments of the invention, the method may further include supplying a torque, and converting the torque into the force.

According to some embodiments of the invention, the detecting may be by measuring a rotation driven by the torque.

According to some embodiments of the invention, the discharging may be at a substantially constant rate for at least 1 minute.

According to some embodiments of the invention, the method may further include releasing a hypodermic needle into the recipient by the apparatus subsequent to the puncturing.

According to some embodiments of the invention, the method may further include releasing a hypodermic needle by the apparatus into the recipient in a direction non-parallel to the applying of the force.

According to some embodiments of the invention, the method may further include releasing a hypodermic needle by the apparatus into the recipient in a direction substantially orthogonal to the applying of the force.

According to some embodiments of the invention, the method may further include sensing by the delivery apparatus of a puncturing of the seal.

According to an aspect of some embodiments of the present invention, there is provided a method for delivering a drug to a recipient with a delivery apparatus, the apparatus may include an internal space initially sealed by a septum for long teen aseptic storage. The delivery apparatus may also include a needle and a processor. The method may include attaching a surface of the delivery apparatus to the recipient. The method may also include puncturing the septum with the needle in response to a command of the processor. The method may also include discharging the drug subsequent to puncturing the septum. The method may also include, detecting a rate of the discharging and adjusting by the processor of the rate of the discharging based on a result of the detecting.

According to some embodiments of the invention, the discharging may be driven by an actuator.

According to some embodiments of the invention, the puncturing may be triggered by the actuator.

According to some embodiments of the invention, the actuator may include a motor. The method may further include transforming a rotational motion of the motor into a linear motion. The discharging may be driven by the linear motion.

According to some embodiments of the invention, the septum may seal a needle opening in a housing of the apparatus.

According to some embodiments of the invention, the needle may include a hypodermic needle. The method may further include inserting the hypodermic needle into the recipient subsequent to the puncturing and prior to the discharging.

According to an aspect of some embodiments of the present invention, there is provided an apparatus wearable by a recipient for delivering a drug to the recipient. The apparatus may include an initially aseptic internal space. The apparatus may also include a septum initially sealing the internal space. The apparatus may also include a controlled rate power source. The apparatus may also include a plunger driven by the controlled rate power source, and a hollow needle. The controlled rate power source may trigger puncturing the septum by the hollow needle, and subsequently, the power source may drive movement of the plunger, discharging the drug from the reservoir.

Unless otherwise defined, all technical and/or scientific terms used herein have the same meaning as commonly understood by one of ordinary skill in the art to which the invention pertains.

Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard disk and/or removable media, for storing instructions and/or data. Optionally, a network connection is provided as well. A display and/or a user input device such as a keyboard or mouse are optionally provided as well.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1 is a flow chart illustrating an exemplary embodiment of a method for unsealing a reservoir and delivering a drug;

FIG. 2A is a perspective external view of an exemplary embodiment of an apparatus for puncturing a septum and delivering a drug;

FIG. 2B is a simplified cutaway view of an exemplary embodiment of an apparatus for puncturing a septum and delivering a drug prior to puncturing the septum;

FIG. 2C is a simplified cutaway view of the embodiment of FIG. 2B after puncturing the septum;

FIG. 2D is a simplified cutaway view of the embodiment of FIG. 2B while delivering the drug;

FIG. 3 is a perspective view of the mechanism of another exemplary embodiment of an apparatus for delivering a drug wherein a septum seals a needle prior to puncturing the septum;

FIG. 3A is a close perspective view of the septum of the embodiment of FIG. 3 prior to puncturing the septum;

FIG. 4 is a perspective view of the mechanism the embodiment of FIG. 3 after puncturing the septum;

FIG. 4A is a close perspective view of the septum of the embodiment of FIG. 3 after puncturing the septum;

FIG. 5 is a cutaway view of a further exemplary embodiment of an apparatus for delivering a drug wherein a septum seals a vial prior to puncturing the septum;

FIG. 6 is a cutaway view of the embodiment of FIG. 5 after puncturing the septum;

Figure 7A:
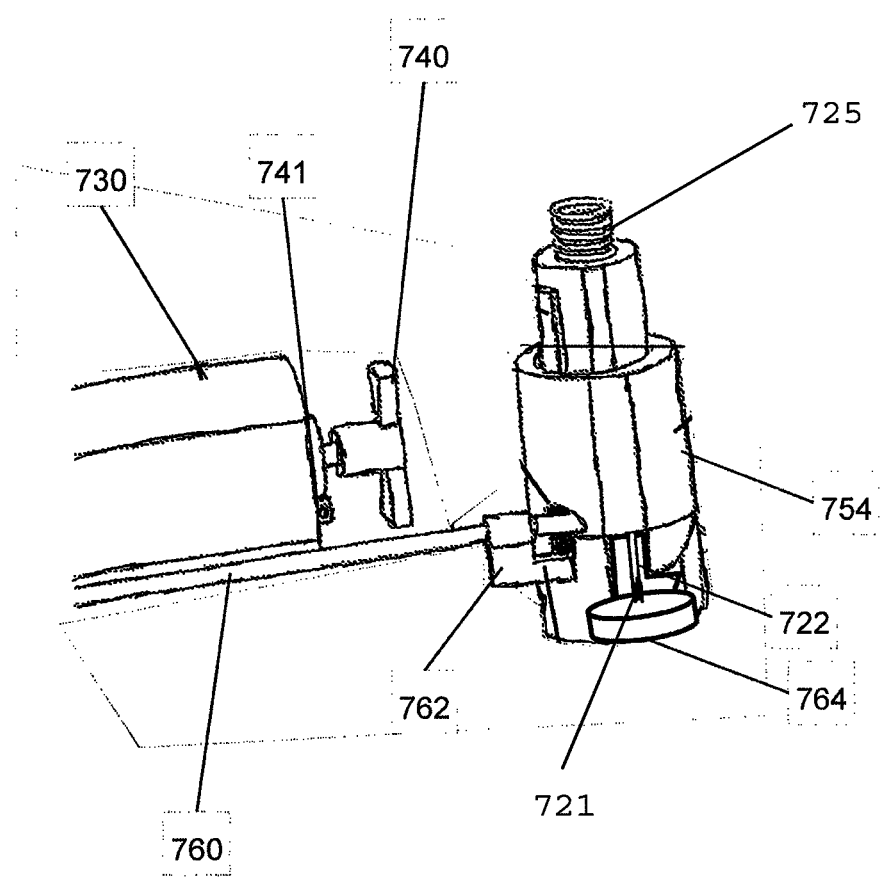
Figure 7B:
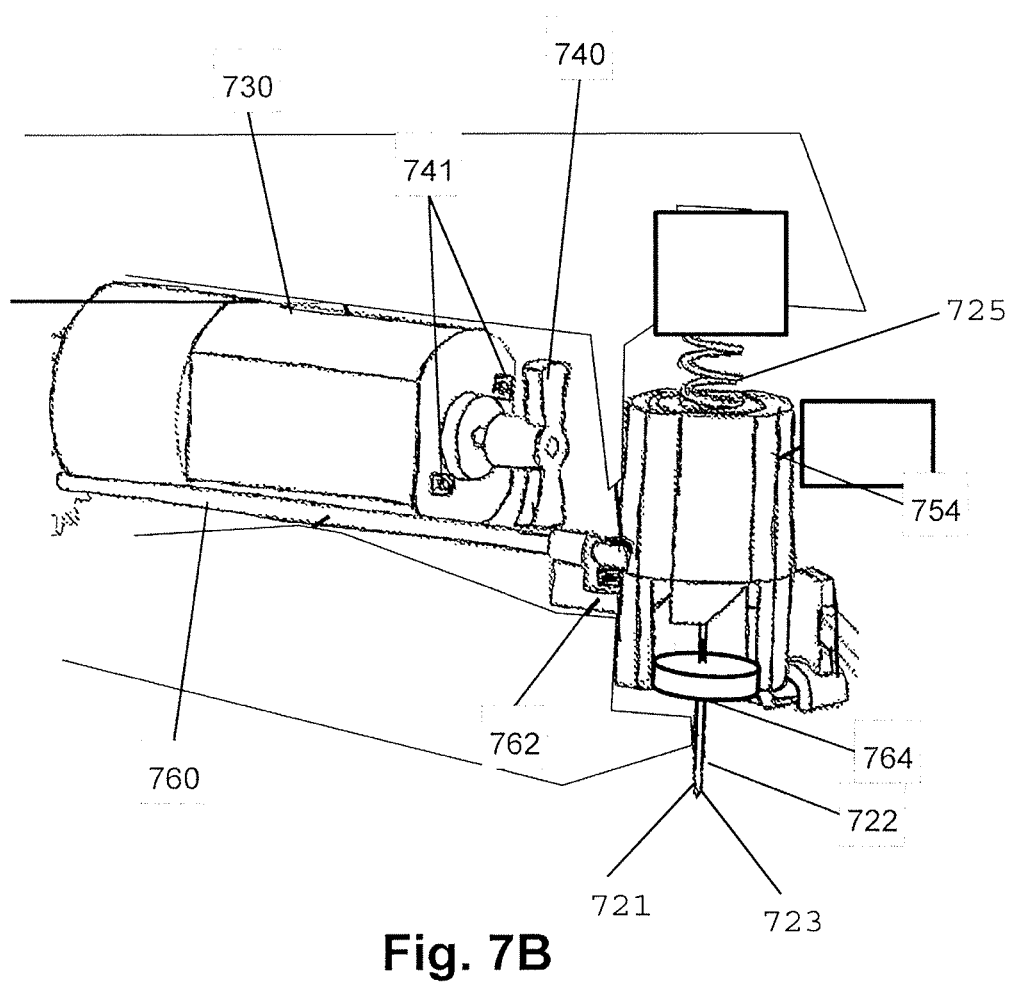
Figure 7C:
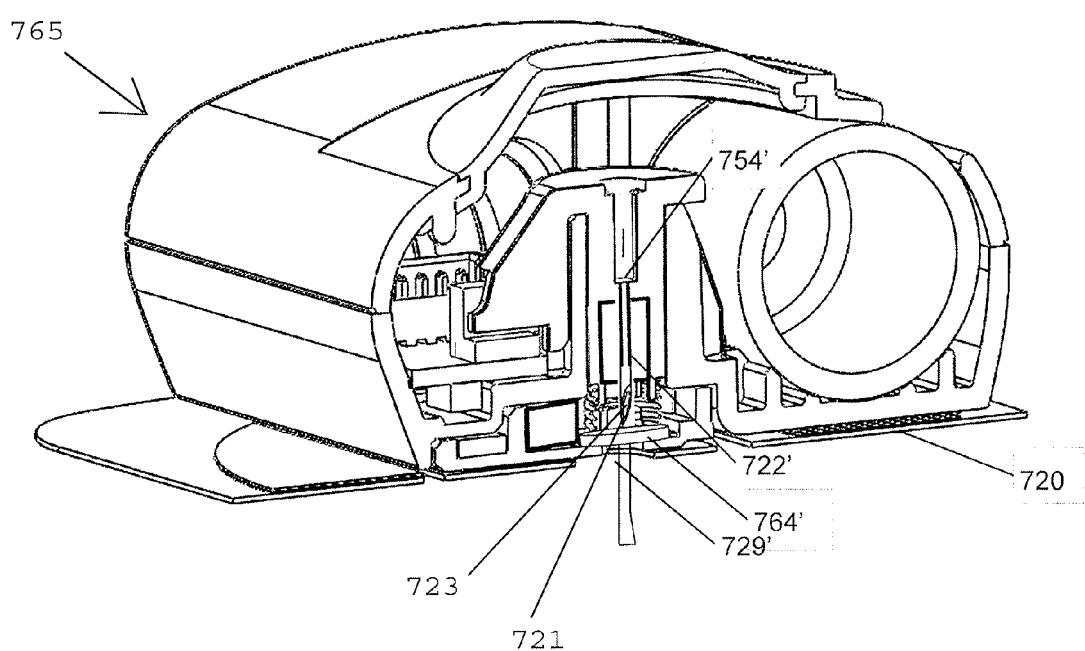
Figure 7D:
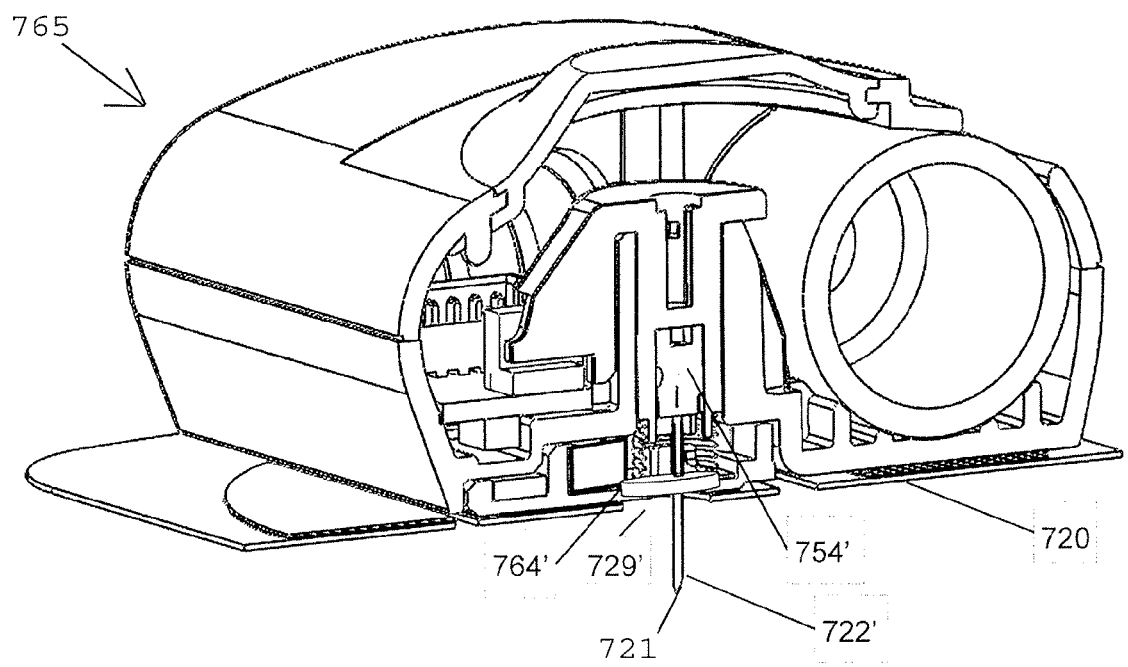
Figure 8:
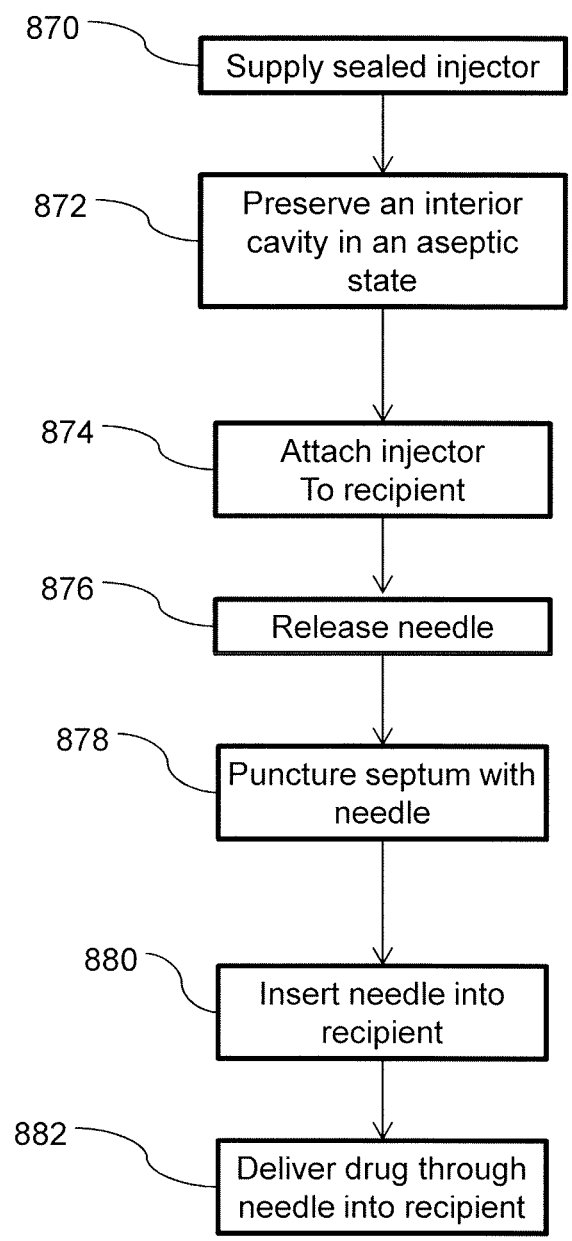

FIG. 7A illustrates a perspective view of an exemplary embodiment of a needle insertion mechanism with a septum, prior to releasing the needle;

FIG. 7B illustrates a perspective view of an exemplary embodiment of a needle insertion mechanism with a septum after releasing of the needle;

FIG. 7C illustrates a cutaway perspective view of an exemplary embodiment of an injection apparatus with a septum and a needle release, previous to releasing the needle;

FIG. 7D illustrates a cutaway perspective view of an exemplary embodiment of a injection apparatus with a septum and a needle release, after releasing the needle, and FIG. 8 is a flowchart illustrating an exemplary embodiment of a method for delivering a drug to a recipient with an initially sealed injector.

DETAILED DESCRIPTION OF THE INVENTION

The present invention, in some embodiments thereof, relates to an apparatus wearable by a recipient and method for delivering a substance to a recipient, more particularly, but not exclusively, to an apparatus with a single-motion controlled-rate power train for sequentially unsealing a reservoir containing a drug and delivering the drug to a recipient.

In some embodiments, an unsealing mechanism may use the existing drive train of the drug discharge device to unseal a drug reservoir. For example, the drive train may include a plunger. Optionally, while the reservoir is sealed, the plunger may drive the syringe along a pathway to an unsealing mechanism. Optionally after unsealing the reservoir, further motion of the plunger may drive discharging of the drug.

In some embodiments, the apparatus may be worn by the recipient. Wearing the apparatus may include, for example, attaching a base of the apparatus to the recipient and/or carrying the apparatus attached to clothing of the recipient and/or strapping the apparatus to the recipient. For example, the base of the apparatus may stick to the skin of the recipient (for example via an adhesive).

In some embodiments, the pathway of movement of the syringe may be parallel to the base of the apparatus.

Controlled Rate Deliver

In some embodiments, the rate of delivery may be controlled. Optionally a drug may be delivered as a bolus injection and/or continuously and/or at a slow rate and/or at a fast rate. Optionally the rate of delivery may be adjustable. In some embodiments, the maximum rate of delivery may optionally be between 10 ml/hr and 100 ml/hr. Optionally, the total delivered volume may be between 0.5 ml and 20 ml. In some embodiments, the total time of delivery may be between 5 seconds and 20 minutes. Optionally, the total time of delivery may be measured from the beginning of delivery until the end of delivery. Optionally, the beginning of deliver may be measured from the time of activation of the apparatus and/or alternatively from the time of attachment of the apparatus and/or alternatively from the time that delivery of the substance begins. Optionally the end of delivery may be measured at deactivation of the apparatus and/or alternatively at the earliest time after which no more of the substance is delivered and/or alternatively when the apparatus is removed from the recipient. Optionally the drug may be delivered in a single dose and/or at a constant rate.

In some embodiments, a drug pump may be a programmable device. For example, the pump may be capable of controlled delivery of a substance according a preprogrammed schedule and/or rate. Alternatively or additionally, the pump may be a smart device capable of changing a delivery schedule according to commands and/or in reaction to changing conditions. Optionally, the device may be capable of stopping and restarting delivery.

Sealed for Long Term Storage and Ready to Use

A drug may require strictly prescribed packaging. Legal, health and safety requirements may include very stringent packaging standards. Packages may need to be aseptic, packaging materials may be strictly limited and package geometry may be very precisely stipulated. For example, when a drug is to be stored for a significant period of time (for example more than 24 hours and/or more than a month) standards may be particularly stringent.

In some cases, it may be inconvenient for the recipient to prepare a drug for delivery and/or to produce a coordinated force to activate a mechanical trigger. For example, the recipient may include a child and/or the medical procedures may induce fatigue or confusion in the recipient (for example chemotherapy). In some cases, the recipient may have a condition that makes it difficult to perform precise tasks (for example rheumatism and/or Parkinson's disease, and/or partial paralysis of the fingers). More generally, opening packaging and then loading the delivery device may be inconvenient and may increase the probability of exposure to contamination or of error or loss of the drug.

It is sometimes desirable to supply a recipient with a delivery device that can be stored. It may also be desirable to supply the delivery device ready to use to deliver a medicine. For example, at a certain time following an outpatient hospital procedure, it may be desirable to deliver a drug to the patient (for example an antidote to chemotherapy agent). Sometimes before a hospital procedure, it may be desirable to deliver a drug to a patient (for example a dye before a radiological diagnostic procedure). A recipient may prefer to receive these drugs from a portable drug pump rather than traveling to a clinic.

In some embodiments, the apparatus may be supplied with a sealed reservoir having an internal space containing a drug. The apparatus may deliver the drug automatically with minimum involvement of the recipient. Optionally, the delivery apparatus may function independently requiring minimal or no cooperation and/or awareness and/or activity of the recipient. For example, a doctor may attach the device to the recipient and the device may take care of delivery of the drug at the proper time without involvement of the recipient. Alternatively or additionally, a recipient may be given a single packaged device and the recipient may be able to take the drug at the required by merely attaching and activating the device.

In some embodiments, a drug reservoir may be sealed by a septum. Optionally, unsealing the reservoir may be by puncturing the septum.

In some embodiments, a drug may be packaged in a vial sealed by a septum. Optionally, the septum may be punctured by inserting a hollow needle through the septum into the vial.

In some embodiments, the drug may be packaged in a syringe. Optionally, a needle of the syringe may be sealed by an insertion into a septum. Optionally, unsealing may be achieved by pushing the needle of the syringe through the septum.

In some embodiments, unsealing a package includes piercing a septum. The septum may include, for example, many kinds of seals including caps, stoppers, plugs, diaphragms and/or partitions of various thicknesses. For example, a septum or a seal may be made from plastic, rubber, silicone, a gel, a metal foil, a polymer and/or a combination thereof.

Portable and/or Low Profile

Optionally, the apparatus may not require conscious carrying by the recipient. Optionally, the apparatus may minimally disturb the recipient. For example, a pump may be small and/or have a low profile. For example, some embodiments of a drug pump may be worn inconspicuously under a recipient's clothing. The height of the apparatus may be less than the square root of the area of the base.

Optionally, the base of the apparatus may be less than 5 cm long and/or less than 5 cm wide. Optionally, the height of the apparatus may be less than 3 cm. Optionally, the total volume of the apparatus may be less than 100-200 ml. Optionally, the mass of the entire apparatus with the substance may be less than 100-200 g. Optionally, the capacity of the reservoir for the substance in the apparatus may be between 5-30 ml). Optionally, the apparatus may be shock proof and/or waterproof.

The term "reservoir" throughout the specification and claims encompasses any container for a drug, such as but not limited to, a cartridge, vial, syringe, bottle, ampoule and many more, and is not limited to any size or shape. Optionally, the reservoir may be packed and/or stored in the injector. Alternatively or additionally, the reservoir may include a cartridge that is stored separately from the delivery device and inserted into the delivery device at a convenient time.

In some embodiments, the apparatus may be easily disposable (for example in municipal garbage).

Caveats

In some embodiments, the apparatus is a medicine pump. The invention is not limited to a drug pump, and may be used for any kind of suitable discharge apparatus, not just by needle piercing the patient, but also transdermally (wherein the substance is metered by the apparatus to a transdermal patch), by spray (wherein the substance is metered by apparatus to a spray nozzle), micro needles array and others.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Flow Chart of a Method of Delivery of a Drug

FIG. 1A is a flow chart illustrating an exemplary method of delivering a drug. In the example, a patient prefers to take a drug injection at home and not remain in a medical institution waiting for a nurse to administer the injection. In the exemplary embodiment, the institution is supplied with a portable preloaded automatic apparatus that can be stored until the recipient needs the drug. When the drug is needed, the apparatus is optionally attached to the recipient and/or activated. Optionally, the apparatus takes care of preliminary activities (for example unsealing the drug reservoir and/or inserting a needle into the recipient). The pump then makes the injection and optionally takes care of preparing itself for disposal.

Figure 1:
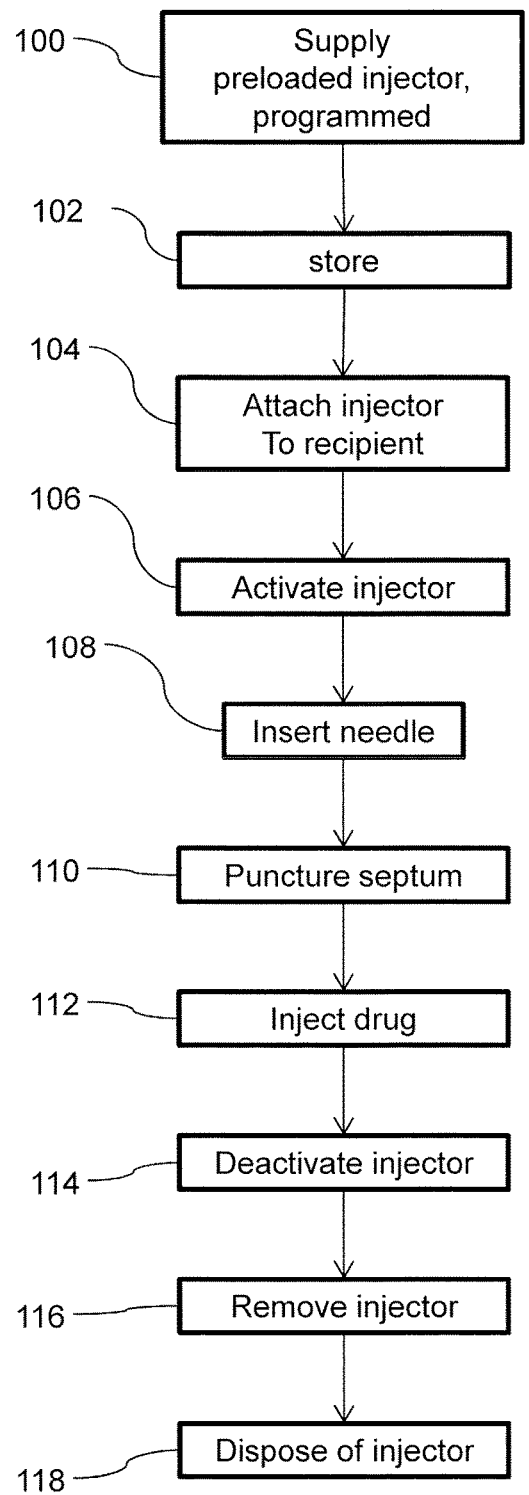

In the exemplary embodiment of FIG. 1, the apparatus is optionally supplied 100 to a medical institution preloaded with the drug and preprogrammed. For example, the substance to be injected may be an antidote to a chemotherapy agent to be injected twelve hours after the therapy. Optionally, the antidote is packaged inside the apparatus in a sealed vial. Optionally, the preloaded apparatus may be stored 102 in a medical institution for a time ranging from a few days to a few months before actually being used. Alternatively or additionally, the apparatus may be supplied to the recipient by, for example, a pharmacy and stored by the recipient for a time ranging from a day to a few months until needed. Alternatively or additionally, the sealed vial may be stored separately from the apparatus. Optionally, vial may be loaded into the apparatus by the distributor and/or by a pharmacist and/or by a medical professional (for example a nurse or a doctor) and/or by the recipient himself.

In the example of FIG. 1, the apparatus is programmed to deliver the entire contents of the reservoir 12 hours after activation in a constant rate injection. Alternatively or additionally, the apparatus may be programmed to deliver a portion of the medicine in a single dose. Optionally the apparatus may be programmed to administer a second dose. Optionally the second dose may be delivered after a fixed time delay and/or the second dose may be delivered on demand of the recipient and/or upon a combination of time delay and command and/or in reaction to some other stimulus.

In the example of FIG. 1, when the apparatus is needed, the apparatus is optionally attached 104 to a recipient. Attachment may be, for example by an adhesive pad on a base surface of the housing of the apparatus. After attachment, the apparatus is activated 106. Alternatively or additionally, the apparatus may be activated first and then attached to the recipient.

Once activated 106, in some embodiments, the apparatus may perform preliminary steps before discharging the drug. Optionally, the preliminary steps may be preprogrammed into the apparatus logic. For example, at a preprogrammed injection time, the apparatus may insert 108 a needle into the recipient. After insertion 108, a reservoir containing the drug may optionally be unsealed 110. For example, the reservoir may include a vial sealed by a septum and the unsealing 110 may be by puncturing the septum. Alternatively or additionally, inserting the needle into the recipient may follow unsealing the reservoir.

In some embodiments, inserting 108 a needle into the recipient and unsealing 110 the reservoir may open a fluid path between the reservoir and the recipient. Once the fluid path is open, the drug is discharged 112 into the recipient at a dosage and rate that is optionally controlled by a controller of the injection apparatus.

In some embodiments, discharge 112 of the drug will start quickly after unsealing 110 the reservoir and/or inserting 108 the needle. For example, in some embodiments discharging 112 will start less than 5 minutes after inserting 108 and/or unsealing 110. In some embodiments, discharging 112 will start less than one minute after inserting 108 and/or unsealing 110. In some embodiments, there may be a short delay after unsealing 110 the reservoir and/or inserting 108 the needle before discharging 112 the substance. In some embodiments, the delay may range between 30 seconds and 5 minutes.

In some embodiments, the apparatus may perform post injection tasks. For example, after the drug has been fully or partially discharged 112, an optional chaser of for example saline solution may be injected. The apparatus may optionally be automatically permanently deactivated 114. For example, deactivation may include retracting the needle. Once the apparatus is deactivated, it may be removed 116 from the recipient and discarded 118. Additionally or alternatively, the apparatus may be removed from the recipient and then disabled. For example, upon removal of an injection apparatus, the needle may be retracted and/or a cover may be deployed to protect the needle.

Optionally, some or all of insertion 108 of the needle and/or unsealing 110 of the reservoir and/or discharging 112 and/or deactivation 114 of the apparatus may be triggered and/or driven by a single motion of an actuator. For example, the actuator may include an electric motor and/or a screw and/or a piston. The motion may optionally be continuous. Alternatively or additionally, the injector may be programmed by the distributor and/or medical personnel (for example a nurse, a doctor or a pharmacist) and/or by the recipient.

An External View of a Low Profile Drug Injector

Figure 2A:
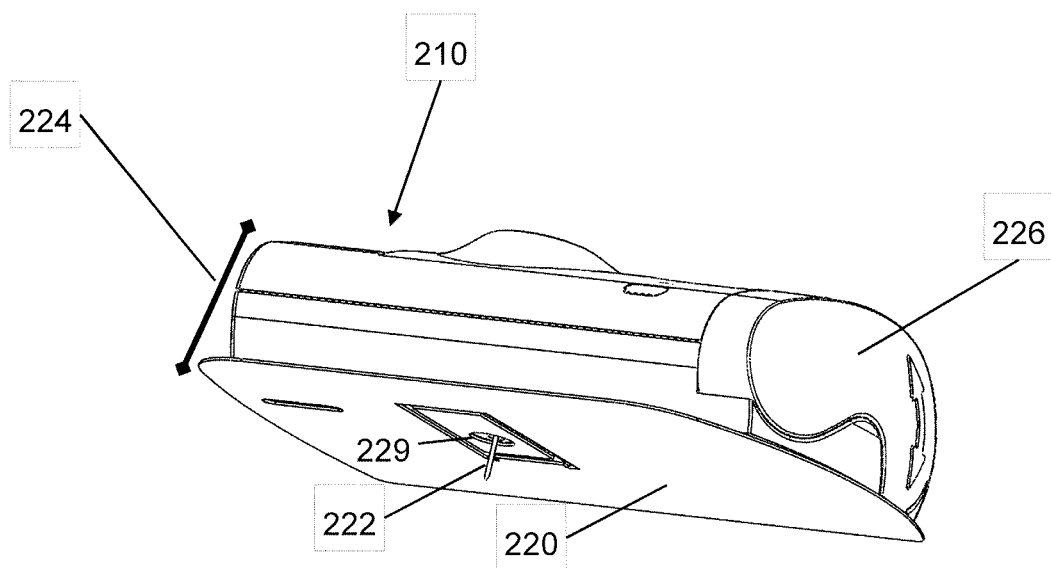

FIG. 2A illustrates an external view of an exemplary embodiment 210 of a drug delivery apparatus (a subcutaneous injector apparatus). During use of embodiment 210, a base surface 220 is stuck to the recipient's skin with an adhesive. A needle 222 extends out a needle opening 229 into a recipient. The drug is discharged via needle 222 into the recipient. Optionally, embodiment 210 is has a large base 220 (for example, the length and width of base 220 is 4 cm by 6 cm) and a low profile (for example, the height 224 of the apparatus is 2 cm). In exemplary embodiment 210, height 224 of the apparatus is less than half the square root of the surface area of base 220. In some embodiments, the height may be less the 1.4 times the square root of the surface area of the base. Embodiment 210 may be stabile when stuck to the recipient's skin. Embodiment 210 may be inconspicuous when worn under clothing.

A locking door 226 may optionally be provided. Door 226 may prevent tampering with the drugs inside the injector. It is noted that although embodiment 210 is typically a one-use item, the electronics, batteries and motor and other elements of the system can be used more than once if desired.

A Schematic Cutaway Illustration of a Drug Pump Puncturing a Septum

Figure 2B:
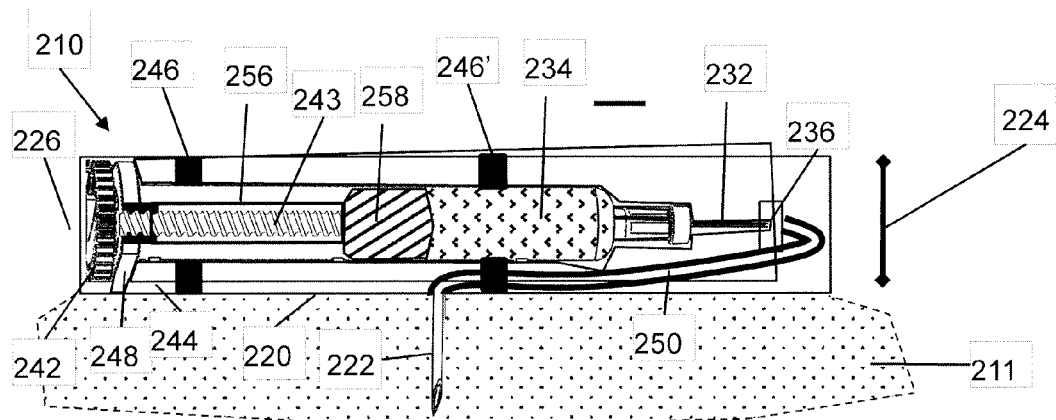
Figure 2C:
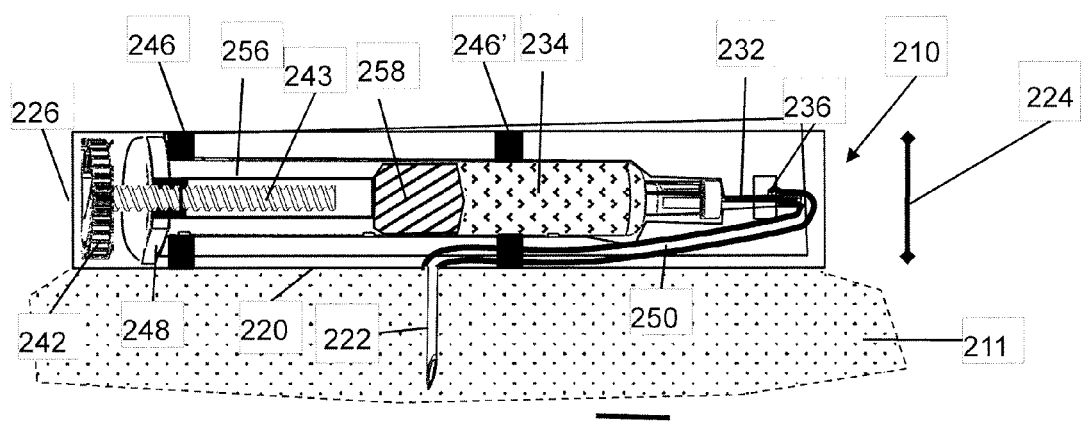
Figure 2D:
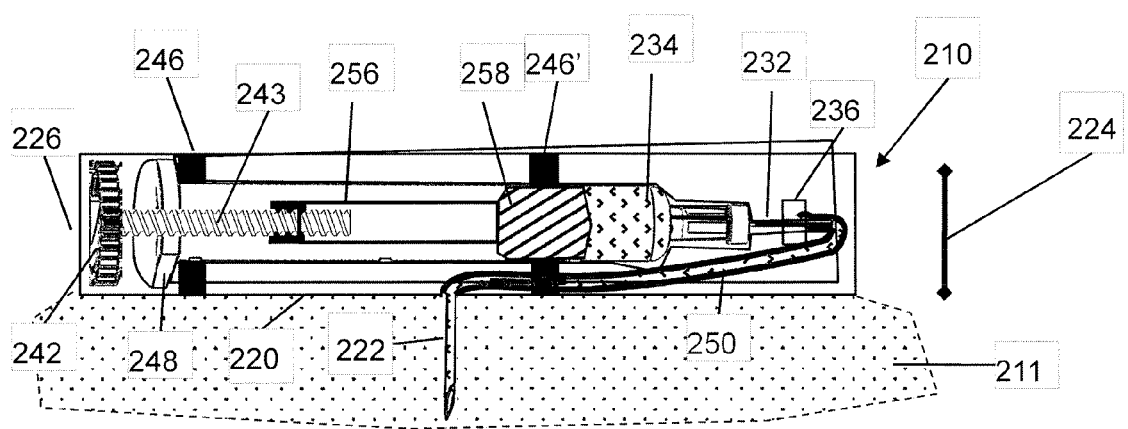

FIGS. 2B-D are schematic cutaway side views illustrating exemplary embodiment 210 of a drug delivery apparatus puncturing a septum and delivering a drug.

FIG. 2B illustrates exemplary embodiment 210 in an initial state. In the example, base 220 of the apparatus is attached to the flesh 211 of a recipient. Hypodermic needle 222 protrudes from base 220 of the apparatus into the flesh 211 of the recipient. Optionally, hypodermic needle 222 may be inserted into the recipient by a release mechanism. In some embodiments, needle 222 protrudes perpendicular to base 220.

In the example, a reservoir 234 is in fluid contact with a hollow needle 232. Optionally, reservoir 234 and consequently needle 232 are held in place, using low friction pads 246 and 246'. In the example, in the initial state, reservoir 234 is placed towards the rear (left side) of the apparatus so that there is a gap 244 between a flange 248 of reservoir 234 and pad 246. In the initial state, needle 232 and consequently reservoir 234 are sealed by a septum 236.

Some embodiments may include a plunger assembly 256 that translates circular motion of a gear 242 into linear motion. In the exemplary embodiment, activating a motor supplies a torque to turn gear 242 and screw 243. Optionally, the housing of the apparatus prevents translation motion of gear 242 and screw 243.

In some embodiments, rotation of screw 243 causes plunger assembly 256 to telescope. While reservoir 234 is sealed, telescoping of assembly 256 pushes reservoir 234 along a path parallel to base 220 of the apparatus. This advances needle 232 through septum 236. Eventually, needle 232 pierces septum 236, unsealing reservoir 234 as shown, for example, in FIG. 2C.

In embodiment 210, the pathway of movement of reservoir 234 is parallel to the base of the apparatus. In embodiment 210, the pathway of movement of a plunger 258 is parallel to the base of the apparatus. In embodiment 210, the long axis of reservoir 234 is parallel to the base of the apparatus. The Length of base 220 of exemplary embodiment 210 is longer than the height 224 of the apparatus. In some embodiments, the long axis of and/or the pathway followed by reservoir 234 may be directed non-parallel to and/or orthogonal to hypodermic needle 222.

In FIG. 2C, the exemplary embodiment is shown with needle 232 puncturing septum 236. In the example, flange 248 is in contact with pad 246 stopping further forward movement of reservoir 234.

In some embodiments, puncturing septum 236 creates a fluid pathway from reservoir 234 through hollow needle 232 and through a canal 250 and through hypodermic needle 222 to flesh 211 of the recipient.

In the exemplary configuration of FIG. 2C, further, telescoping of assembly 256 advances a plunger 258 inside of reservoir 234 as illustrated, for example, in FIG. 2D. Advancement of plunger 258 discharges the drug out of needle 232, canal 250 and needle 222 into flesh 211 of the recipient.

A Syringe Reservoir with a Needle for Puncturing a Septum

Figure 3:
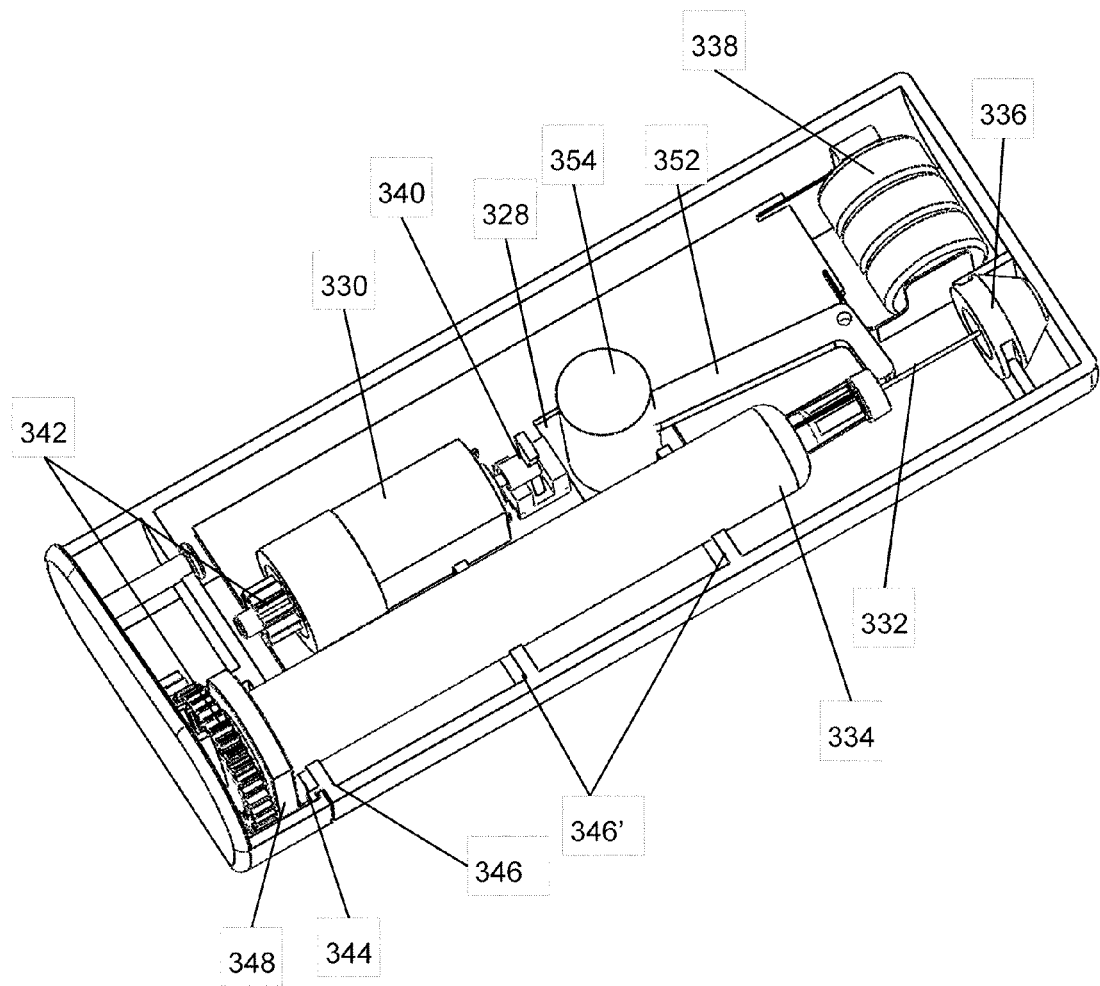
Figure 3A:
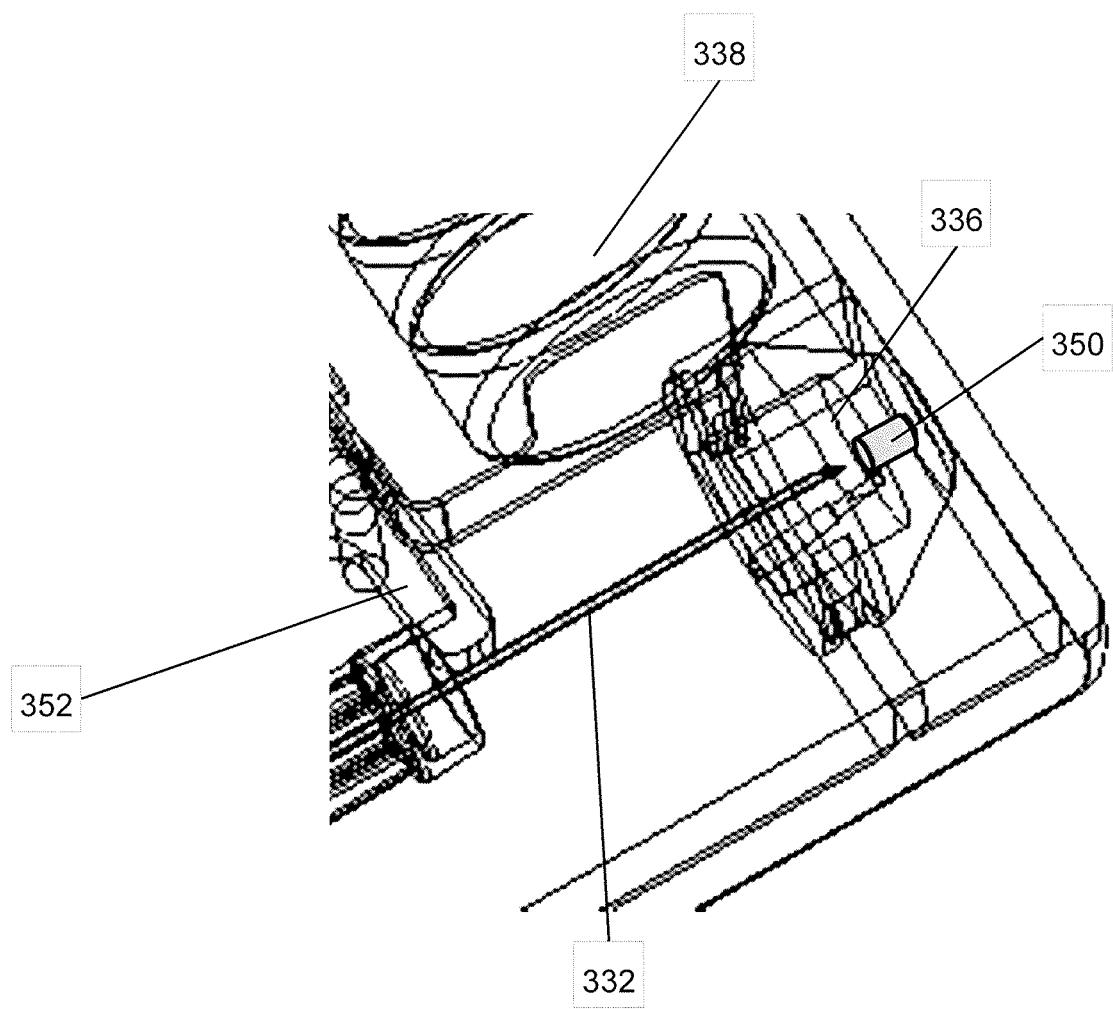
Figure 4:
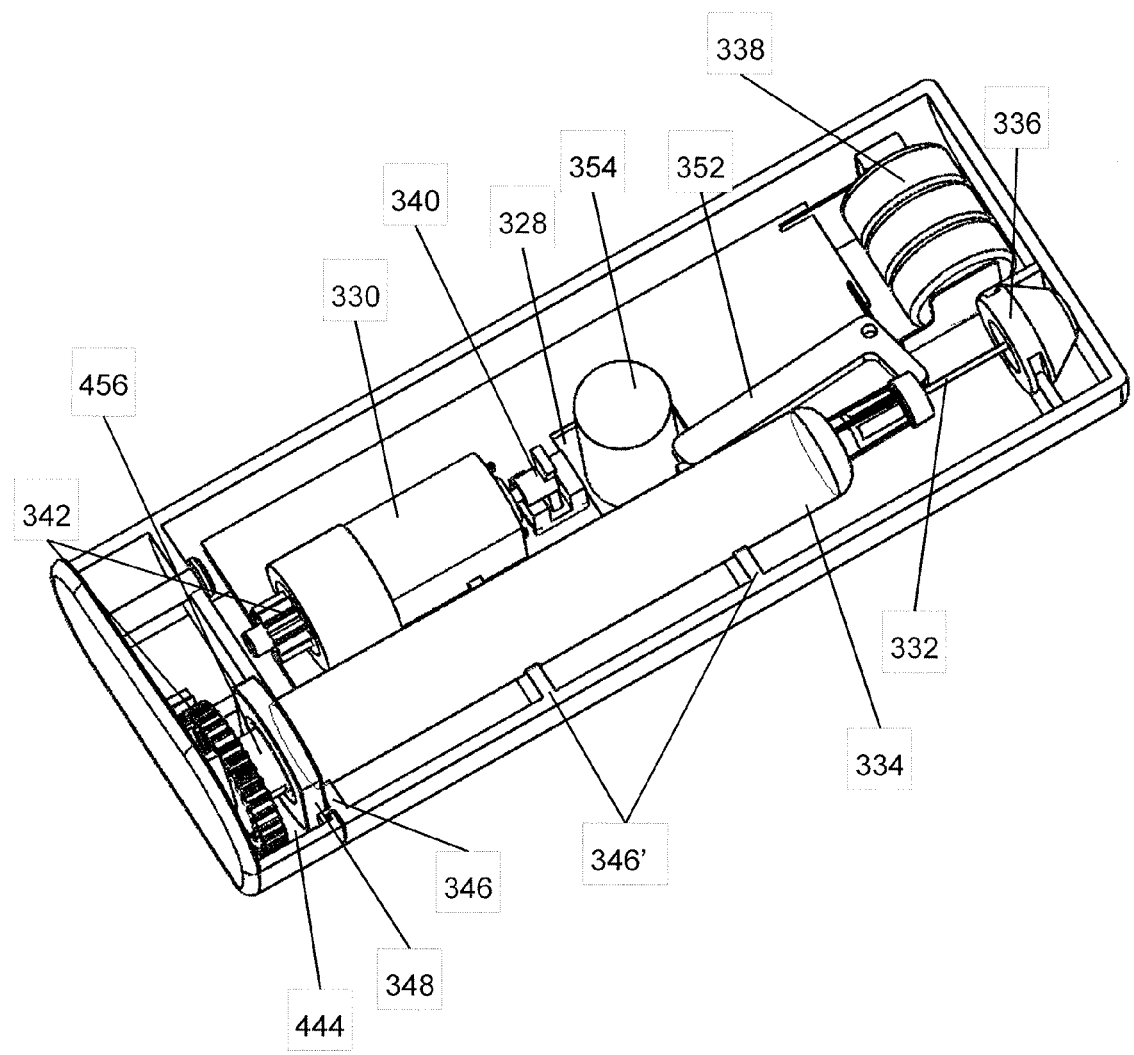
Figure 4A:
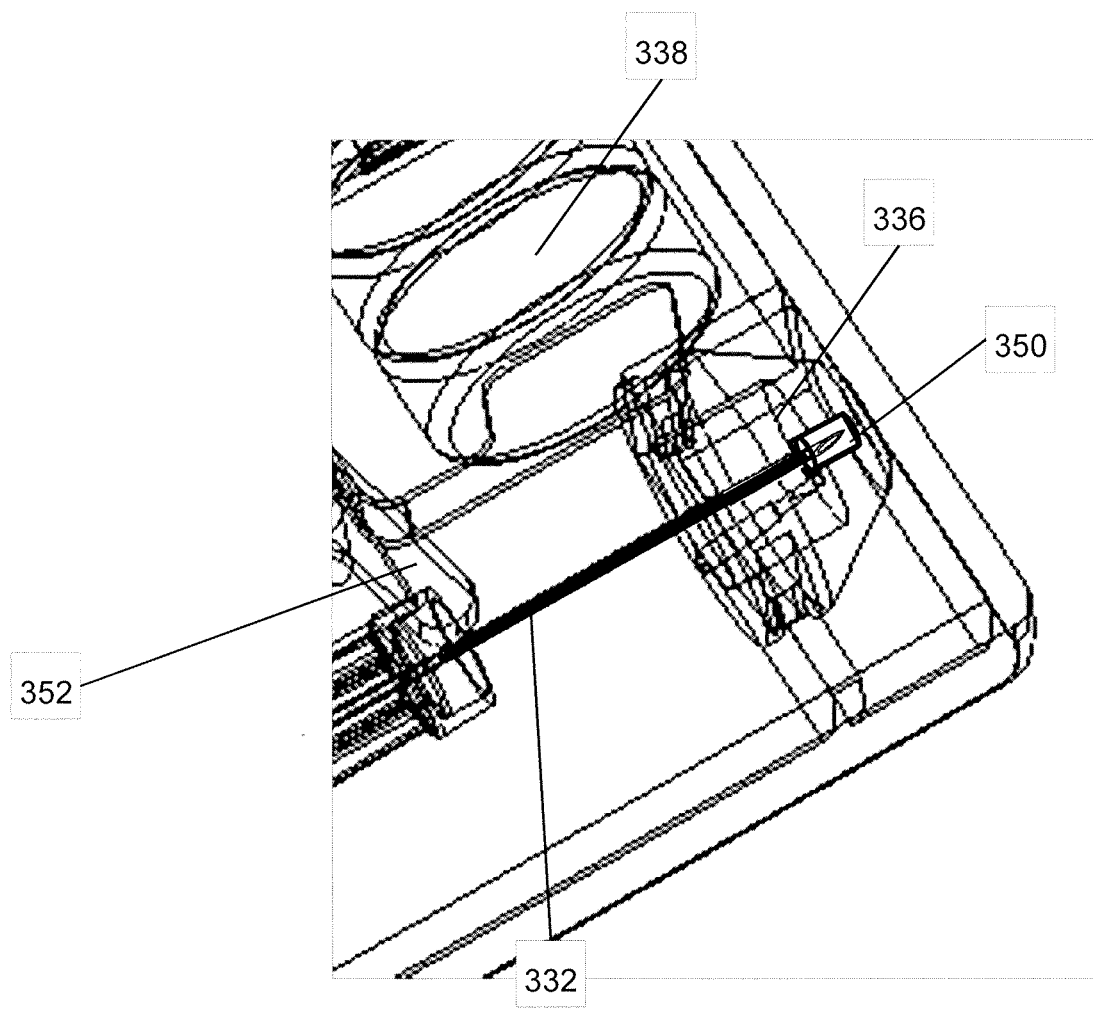

FIGS. 3, 3A, 4 and 4A illustrate another exemplary embodiment 310 of a drug delivery apparatus. In embodiment 310, a syringe needle 332 is mounted to a reservoir 334. In FIGS. 3 and 3A needle 332 is shown sealed by an optional septum 336. In FIGS. 4 and 4A needle 332 is shown puncturing septum 336 to unseal reservoir 334.

FIGS. 3 and 4 illustrate an optional programmable controller 328 capable of directing an optional power actuator 330 for powering discharging of a substance. In addition, FIGS. 3, 3A, 4 and 4A illustrate how actuator 330 may optionally drive puncturing of septum 336 and/or trigger insertion of a needle into the recipient.

In some embodiments, controller 328 may be a programmable electronic processor. Controller 328 may optionally include a memory.

In some embodiments, actuator 330 may include a direct current (DC) electric motor. Power for controller 328 and actuator 330 may be supplied by a power supply 338 (for example batteries). Controller 328 may optionally direct actuator 330 by pulse width modulation (PWM). Alternatively or additionally, actuator 330 may include a brushless DC servo (for example a stepper motor) directed by controller 328. In some embodiments, the rate of rotation of actuator 330 may be adjustable. The rate of discharge of the drug may correspond to the rate of rotation of the actuator 330. Optionally, rate of rotation of the actuator 330 may be adjusted by programming controller 328 and/or by a user interface (for example a dial and/or button) on the apparatus.

Embodiment 310 includes an optimal rotation sensor 340. In some embodiments rotation sensor 340 may include an optical sensor that detects movements of a paddle. Alternatively or additionally, rotation sensor may include a Hall Effect sensor or the like. Optionally, if actuator 330 fails to rotate and/or rotates too slowly upon application of power, controller 328 may notify the recipient of a malfunction. Other malfunctions that may be detected include not enough voltage, not enough current, too much current, and/or too fast rotation.

In FIGS. 3 and 3A, a drug reservoir 334 is shown in a sealed configuration. Reservoir 334 is held in place for example by low friction pads 346 and 346'. In the sealed configuration, needle 332 is optionally sealed by septum 336, for example, as illustrated in FIG. 3A.

In some embodiments, when reservoir 334 is in the sealed configuration, a gap 344 exists between a flange 348 of reservoir 334 and friction pad 346.

Figure 5:
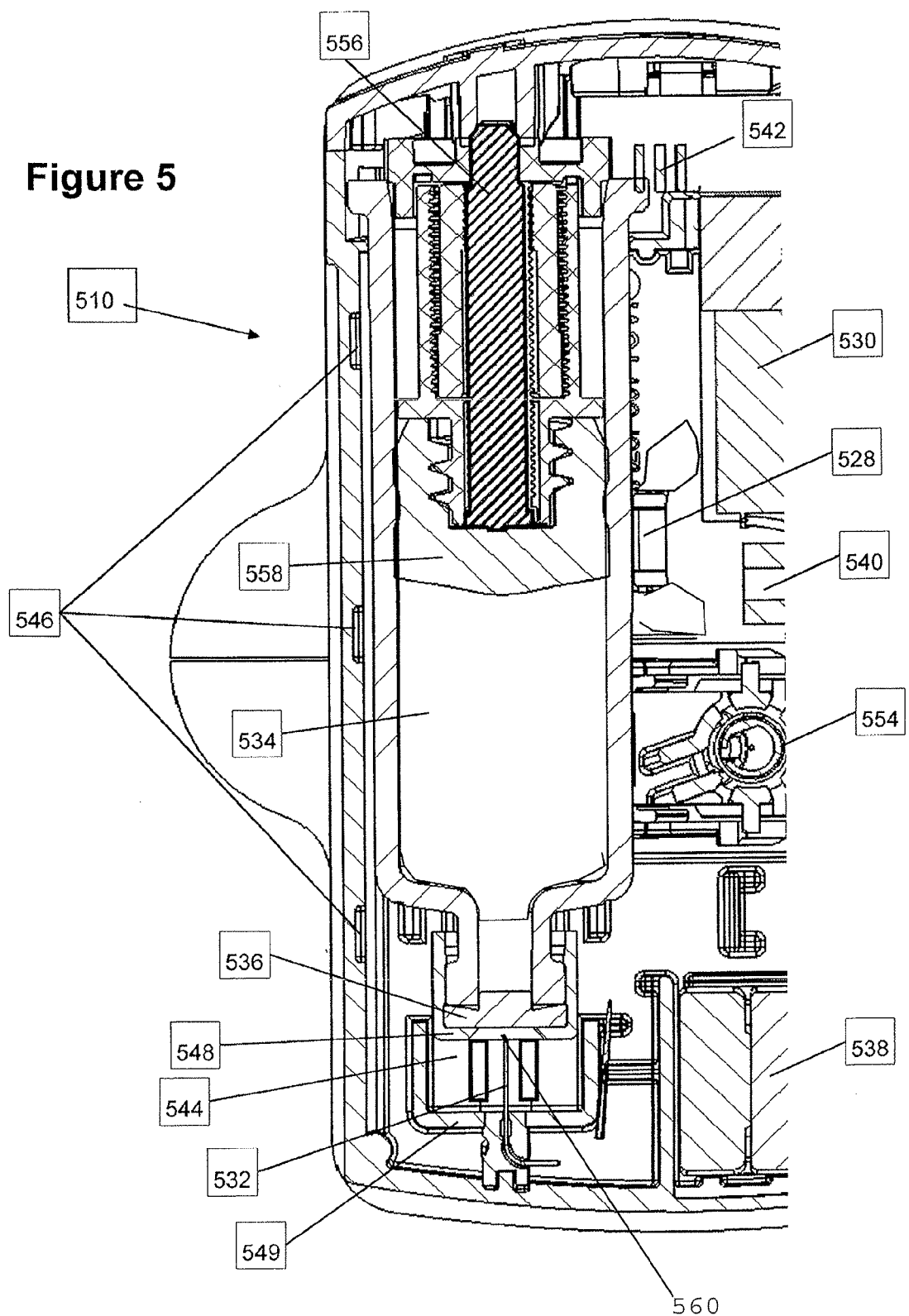
Figure 6:
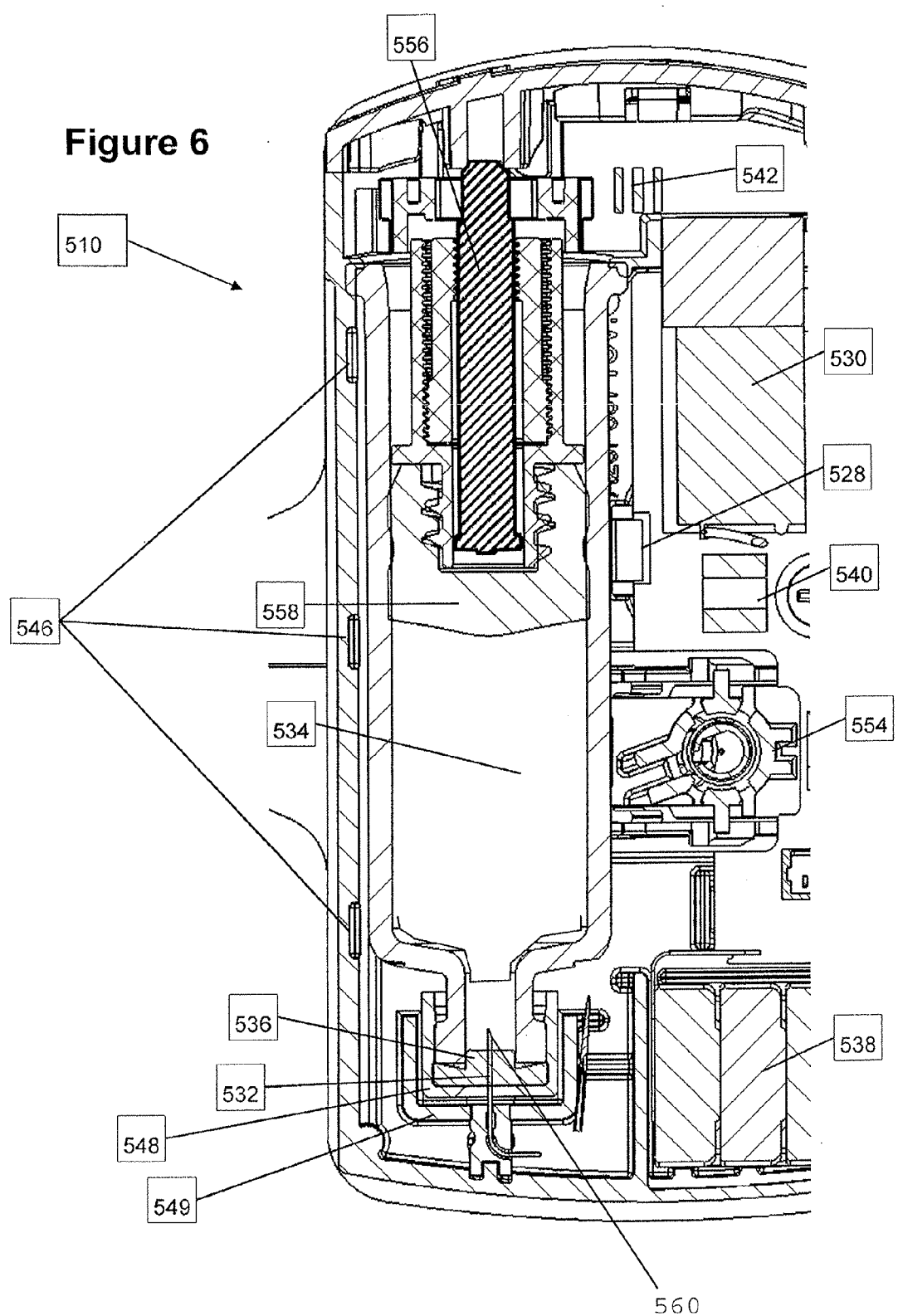

In some embodiments, a transmission including gears 342 and a drive train (not show) connect actuator 330 to a telescoping plunger assembly (for example see plunger assembly 456 FIG. 4) located inside reservoir 334. A more detailed view of an exemplary embodiment of a plunger assembly 556 is shown in FIGS. 5 and 6. Alternatively or additionally, a plunger assembly may include a linear actuator. In exemplary embodiment 310, the transmission includes a gear, but alternatively or additionally, it could include another coupling element for transmitting rotary motion, such as a friction wheel. Optionally rotation of actuator 330 drives expansion of telescoping plunger assembly 456. Alternatively or additionally, the drive mechanism may include an expanding gas chamber. For example, expanding gas may be produced by an electrolytic cell and/or by a chemical reaction. Alternatively or additionally, the reservoir may have flexible walls. Optionally, discharge may include deforming and/or squeezing the reservoir.

In embodiment 310, while reservoir 334 is in the sealed configuration of FIGS. 3 and 3A, expansion of plunger assembly 456 drives reservoir 334 and needle 332 forward. Optionally, forward motion stops when flange 348 contacts friction pad 346, which acts as a stop along the pathway of movement of reservoir 334.

In some embodiments, forward movement of reservoir 334 pushes needle 332 through septum 336 putting the apparatus into the discharge configuration, for example, as illustrated in FIG. 4. In the discharge configuration, a gap 444 has formed behind flange 348. The rear end of telescoping plunger assembly 456 can be seen in gap 444. In the discharge configuration, needle 332 has fully punctured septum 336, unsealing reservoir 334. A fluid path exists from reservoir 334 through needle 332 to a canal 350.

In embodiment 310, the pathway of movement of reservoir 334 is parallel to the base of the apparatus. In embodiment 310, the pathway of movement of plunger assembly 456 is parallel to the base of the apparatus. In embodiment 310, the long axis of reservoir 334 is parallel to the base of the apparatus. The base of the apparatus is longer than the height of the apparatus.

Embodiment 310 includes an optional trigger arm 352 for triggering a needle release 354. As reservoir 334 moves forward it displaces arm 352 causing needle release 354 to insert a hypodermic needle (not shown) into the recipient. A tube (not shown) supplies a fluid pathway from canal 350 to the hypodermic needle. In the discharge configuration, there is a fluid pathway from reservoir 334 to the recipient. Optionally, the hypodermic needle may be inserted into the recipient either before or after completing puncturing of septum 336. Alternatively or additionally, controller 328 may directly control needle release 354. Optionally, the direction of release of the needle may be non-parallel and/or orthogonal to the direction of movement of plunger assembly 456.

In the example of embodiment 310, telescoping plunger assembly 456 includes a threaded member to convert rotational motion of actuator 330 into expansion and translational motion of the plunger assembly 456. Optionally, in embodiment 310 rotation of sensor 340 may be directly proportional translational movement. In embodiment 310, measurements of rotation can be used to sense the position of the translational mechanism. By means of measurements of the rotation of actuator 330, controller 328 optionally tracks the location of telescoping plunger assembly 456 and/or of reservoir 334 and/or of needle 332. Optionally the rate of discharge of the drug may be detected by measuring a rate of rotation of sensor 340. Optionally, the state of the septum 336 (for example whether plunger assembly 456 has advanced far enough to puncture septum 336) and/or the cumulative volume of medicine discharged may be sensed based on the cumulative number of revolutions of rotation sensor 340.

In embodiments 310, when reservoir 334 is in the discharge configuration, friction pad 346 prevents further forward motion of reservoir 334. As stated above, in the discharge configuration, there is a fluid flow path from reservoir 334 into the recipient. Further expansion of the plunger assembly 456 forces the plunger assembly 456 into reservoir 334 discharging the contents of reservoir 334 out needle 332 into canal 350 and out canal 350 through the hypodermic needle into the recipient.

A Reservoir where a Hollow Needle is Inserted into a Vial Through a Septum

FIG. 5 is a cutaway illustration of an exemplary embodiment 510 of a drug delivery apparatus. In embodiment 510, a reservoir is sealed by a septum. Optionally, the septum is punctured by driving the reservoir toward a hollow needle until a needle point 560 of the needle punctures the septum. Upon puncturing the septum, the point 560 of the needle enters the reservoir. Subsequently, the hollow of the needle provides for fluid communication between the reservoir and the external environment.

Embodiment 510 includes a reservoir 534 sealed by a cartridge seal or septum 536. Optionally, reservoir 534 may be placed a bit away from a hollow needle 532 in a sealed configuration (For example, as illustrated in FIG. 5). Reservoir 534 may be held in place, for example, using low friction pads 546, with needle 532 against and/or partially inserted into and/or adjacent to septum 536.

In embodiment 510, activating a motor 530 may cause a telescoping assembly 556 to telescope, pushing a plunger 558 into reservoir 534. In the example of embodiment 510, telescoping plunger assembly 556 includes concentrically mounted threaded members to convert rotational motion of an actuator, motor 530, into expansion of telescoping assembly 556 and translation of plunger 558. Because reservoir 534 is sealed, translation of plunger 558 advances reservoir 534 against needle 532, puncturing septum 536 (as shown, for example, if FIG. 6). Optionally, reservoir 534 translates forward until a cap 548 of reservoir 534 crosses a gap 544 and contacts a stop 549.

Puncturing septum 536 creates a fluid flow path between reservoir 534 and the recipient's body. The flow path allows further translation of plunger 558 to produce fluid flow out needle 532 and through a tube (not shown) into a hypodermic needle (not shown) and into the recipient.

Embodiment 510 includes further optional components, for example batteries 538, and a needle release 554, and a rotation sensor 540, and a controller 528, and a transmission 542.

A Septum Preserving Aseptic Conditions of a Hypodermic Needle

FIGS. 7A and 7B illustrate perspective views of an exemplary embodiment of a needle insertion mechanism 754 with a needle opening septum 764. Needle opening septum 764, seals a needle opening, preserving aseptic conditions inside an injector (as illustrated, for example, in FIG. 7C).

In some embodiments, when the apparatus is attached to a recipient, when needle 722 is released, it may optionally pass through needle opening septum 764 (as illustrated, for example, in FIG. 7B) and be inserted into the flesh of the recipient.

In some embodiments, prior to release, needle 722 may be partially inserted into needle opening septum 764 (for example as illustrated in FIG. 7A). While partially inserted, the distal opening 723 at the needle tip 721 of needle 722 may be sealed by needle opening septum 764. Needle 722 may be in fluid communication with a drug reservoir. Sealing needle 722 may seal the reservoir. Alternatively or additionally, prior to release, a hypodermic needle 722' may be held clear of a needle opening septum 764', as illustrated, for example in FIG. 7C).

In the example of FIGS. 7A and 7B, a motor 730 rotates a shaft 760. Rotation of shaft 760 optionally causes a threaded arrester 762 to slide out of an opening in insertion mechanism 754 releasing needle 722. A biasing member 725 biases the needle 722 toward the released position (FIG. 7B) such that when the threaded arrester 762 disengages from the insertion mechanism, the needle is transferred to the released position. In some embodiments, motor 730 may also trigger unsealing a reservoir and discharging of a drug (as illustrated, for example, above). An optional rotation sensor includes sensors 741, which sense revolutions of a paddle 740.

In some embodiments, needle opening septum 764' may be fixed to the housing 765 of the injection apparatus. For example, FIGS. 7C and 7D are cutaway perspective illustrations of an exemplary embodiment where needle opening septum 764' is connected to a base 720 of the housing 765 of the injection apparatus. FIG. 7C illustrates the exemplary embodiment prior to release of a needle 722' by a release 754'. In the illustration, needle opening 729' is sealed by needle opening septum 764'. FIG. 7D illustrates the exemplary embodiment after release of needle 722' and after needle 722' punctures needle opening septum 764'.

FIG. 8 is a flow chart illustration of an exemplary embodiment of a method for delivering a drug to a recipient. In some embodiments, an injector apparatus may be supplied 870 in a sealed state. Optionally in the sealed state, an internal space of the injector may be preserved 872 in an aseptic state by a septum. Optionally, a hypodermic needle may be stored in the aseptic internal space of the injector.

In some embodiments, the apparatus may be attached 874 to the recipient while still in the sealed state. For example, a base of the apparatus may be stuck to the recipient using an adhesive.

In some embodiments, there may be a release mechanism. The mechanism may release 876 the needle. For example, the needle may be released 876 after attachment 874 of the apparatus to the recipient. Optionally upon release 876, the needle may puncture 878 the septum.

In some embodiments, the needle may continue through the septum, through a needle opening in the base of the apparatus and be inserted 880 into the recipient.

Once the needle is inside the recipient, a drug may optionally be delivered 882 through the needle into the recipient.

Caveats

It is expected that during the life of a patent maturing from this application many relevant technologies will be developed and the scope of the terms is intended to include all such new technologies a priori.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. A wearable drug delivery apparatus for administering a drug to a recipient, the drug delivery apparatus comprising:
    a housing having a base surface configured to be positioned proximate the subject's skin, the base surface having a needle opening therein;
    a controlled rate power actuator;
    a cartridge positioned within the housing, having a longitudinal axis being substantially parallel to the base surface, the cartridge containing the drug therein and having one of a septum or a piercing needle and the housing having the other of the septum and the piercing needle, the cartridge being movable by the power actuator from a sealed position, wherein the piercing needle is sealed by the septum, to a discharge position, wherein the piercing needle punctures through the septum;
    a plunger movably mounted in the cartridge, the plunger being movable by the power actuator along the longitudinal axis;
    an injection needle fluidly connectable to the cartridge and having a needle tip including an opening, the needle tip being movable by a biasing member from a retracted position, wherein the needle tip is located within the housing, to a released position, wherein the needle tip extends through the needle opening and is located outside of the housing;
    a trigger arm triggering the release of the needle tip into the released position when the trigger arm is moved by the cartridge as the cartridge is moved from the sealed position to the discharge position; and
    an injection needle septum positioned in the housing;
    wherein the needle tip is inserted in the injection needle septum, sealing the needle tip opening in the retracted position, and the needle tip penetrates through the injection needle septum in the released position.

2. The drug delivery apparatus of claim 1, wherein the injection needle septum is positioned within the needle opening.

3. The drug delivery apparatus of claim 1, wherein the needle tip is oriented substantially perpendicular to the base surface.

4. The drug delivery apparatus of claim 1, wherein the needle tip is injected into the subject's skin in the released position.

* * * * *